US007371539B2

(12) United States Patent
Church et al.

(10) Patent No.: US 7,371,539 B2
(45) Date of Patent: May 13, 2008

(54) TARGETED POLYPEPTIDE DEGRADATION

(75) Inventors: George M. Church, Brookline, MA (US); Daniel M. Janse, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/003,103

(22) Filed: Dec. 3, 2004

(65) Prior Publication Data

US 2005/0152888 A1    Jul. 14, 2005

Related U.S. Application Data

(60) Provisional application No. 60/526,490, filed on Dec. 3, 2003.

(51) Int. Cl.
*G01N 33/53* (2006.01)
*C07K 1/10* (2006.01)

(52) U.S. Cl. .................................. 435/7.6; 530/350
(58) Field of Classification Search ................ 435/7.6; 530/350
See application file for complete search history.

(56) References Cited

U.S. PATENT DOCUMENTS

| | | | |
|---|---|---|---|
| 4,522,811 A | 6/1985 | Eppstein et al. ................ | 514/2 |
| 4,736,866 A | 4/1988 | Leder et al. .................... | 800/1 |
| 4,870,009 A | 9/1989 | Evans et al. ................... | 435/70 |
| 4,873,191 A | 10/1989 | Wagner et al. ............. | 435/172.3 |
| 5,223,409 A | 6/1993 | Ladner et al. ............. | 435/69.7 |
| 6,217,864 B1 * | 4/2001 | Coffino et al. ............ | 424/94.63 |

FOREIGN PATENT DOCUMENTS

| | | |
|---|---|---|
| WO | WO 90/11354 | 10/1990 |
| WO | WO 91/01140 | 2/1991 |
| WO | WO 92/0968 | 6/1992 |
| WO | WO 93/04169 | 3/1993 |

OTHER PUBLICATIONS

Alberts et al., "Macromolecules: Structure, Shapes and Information," *Molecular Biology of the Cell*, Chapter 3, pp. 88-91, 3d edition, Garland Publishing (1994).
Bachmair et al., "In Vivo Half-Life of a Protein Is a Function of its Amino-Terminal Residue," *Science*, 234:179-186 (1986).
Baron and Bujard, "Tet Repressor-Based System for Regulated Gene Expression in Eukaryotic Cells: Principles and Advances," *Methods Enzymol.* 327:401-421 (2000).
Belshaw et al., "Controlling protein association and subcellular localization with a synthetic ligand that induces heterodimerization of proteins," *Proc. Natl. Acad. Sci. USA*, 93:4604-4607 (1996).
Benaroudj et al., "PAN, the proteasome-activating nucleotidase from archaebacteria, is a protein-unfolding molecular chaperone," *Nat. Cell Biol.*, 2:833-839 (2000).

Bochtler et al., "Crystal structure of heat shock locus V (HsIV) from *Excherichia coli*," *Proc. Natl. Acad. Sci. U.S.A.* 94:6070-6074 (1997).
Bochtler et al., "The Proteasome," *Ann. Rev. Biophys. Biomol. Struct.* 28:295-317 (1999).
Bochtler et al., "The structures of HsIU and the ATP-dependent protease HsIU-HsIV," *Nature* 403:800-805 (2000).
Bradley, "Production and analysis of chimaeric mice," *Teratocarcinomas and Embryonic Stem Cells*: A Practical Approach, E. J. Robertson, ed, IRL, Oxford, pp. 113-151 (1987).
Bradley, "Modifying the mammalian genome by gene targeting," *Current Opinion in Biotechnology* 2:823-829 (1991).
Braun et al., "The base of the proteasome regulatory particle exhibits chaperone-like activity," *Nat. Cell Biol.*, 1:221-226 (1999).
Carrell et al., "A Novel Procedure for the Synthesis of Libraries Containing Small Organic Molecules," *Angew. Chem. Int. Ed. Engl.*, 33:2059-2061 (1994).
Carrell et al., "A Solution-Phase Screening Procedure for the Isolation of Active Compounds from a Library of Molecules," *Angew. Chem. Int. Ed. Engl.*, 33:2061-2065 (1994).
Cho et al., "An Unnatural Biopolymer," *Science* 261:1303-1305 (1993).
Coffino, "Regulation of Cellular Polyamines by Antizyme," *Nat. Rev. Mol. Cell Biol.*, 2:188-194 (2001).
Colas et al., "Targeted modification and transportation of cellular proteins," *Proc. Natl. Acad. Sci. USA* 97(25):13720-13725 (2000).
Cull et al., "Screening for receptor ligands using large libraries of peptides linked to the C terminus of the *lac* repressor," *Proc. Natl. Acad. Sci. USA*, 89:1865-1869 (1992).
Cwirla et al., "Peptides on phage: A vast library of peptides for identifying ligands," *Proc. Natl. Acad. Sci.*, USA 87:6378-6382 (1990).
David et al., "Proteasomal degradation of tau protein," *J. Neurochem.*, 83:176-185 (2002).
Deveraux et al., "A 26 S Protease Subunit that Binds Ubiquitin Conjugates," *J. Biol. Chem.*, 269(10):7059-7061 (1994).
Devlin, "Random Peptide Libraries: A Source of Specific Protein Binding Molecules," *Science*, 249:404-406 (1990).
DeWitt et al., "'Diversomers': An approach to nonpeptide, nonoligomeric chemical diversity," *Proc. Natl. Acad. Sci. USA*, 90:6909-6913 (1993).
Dick et al., "Proteolytic Processing Ovalbumin and β-galactosidase by the Proteasome to Yield Antigenic Peptides," *J. Immunol.*, 152:3884-3894 (1994).

(Continued)

*Primary Examiner*—Anne Marie Wehbe
*Assistant Examiner*—Fereydoun G. Sajjadi
(74) *Attorney, Agent, or Firm*—Banner & Witcoff, Ltd.

(57) ABSTRACT

This invention pertains to compositions, methods, cells and organisms useful for selectively localizing polypeptides to the proteasome for degradation. Therapeutic methods and pharmaceutical compositions for treating disorders associated with the expression and/or activity of a polypeptide by targeting these polypeptides for degradation, as well as methods for targeting therapeutic polypeptides for degradation and/or activating therapeutic polypeptides by degradation are provided. The invention provides methods for identifying compounds that mediate proteasome localization and/or polypeptide degradation. The invention also provides research tools for the study of protein function.

7 Claims, 5 Drawing Sheets

OTHER PUBLICATIONS

Erb et al., "Recursive deconvoluation of combinatorial chemical libraries," *Proc. Natl. Acad. Sci. USA*, 91:11422-11426 (1994).

Farrar et al., "Activation of the Raf-1 kinase cascade by coumermycin-induced dimerization," *Nature*, 383(6596):178-181 (1996).

Felici, "Selection of Antibody Ligands from a Large Library of Oligopeptides Expressed on a Multivalent Exposition Vector," *J. Mol. Biol.*, 222:301-310 (1991).

Fire et al., "Potent and specific genetic interference by double-stranded RNA in *Caenorhabditis elegans*," *Nature*, 391:806-811 (1998).

Fodor, "Multiplexed biochemical assays with biological chips," *Nature*, 364:555-556 (1993).

Gallop et al., "Applications of Combinatorial Technologies to Drug Discovery, . . . ," *J. Med. Chem.*, 37(9):1233-1251 (1994).

Glaever et al., "Functional profiling of the *Saccharomyces cerevisiae* geneome," *Nature*, 418:387-391 (2002).

Groll et al., "Structure of 20S proteasome from yeast at 2.4Å resolution," *Nature*, 386:463-471 (1997).

Groll et al., "A gated channel into the proteasome core particle," *Nat. Struct. Biol.*, 7(11):1062-1067 (2000).

Groll and Huber, "Substrate access and processing by the 20S proteasome core particle," *Int. J. Biochem. Cell Biol.*, 35:606-616 (2003).

Güldener et al., "A new efficient gene disruption cassette for repeated use in budding yeast," *Nucleic Acids Res.*, 24(13)2519-2524 (1996).

Harvey et al., "Forced engagement of a RNA/protein complex by a chemical inducer of dimerization to modulate gene expression," *Proc. Natl. Acad. Sci. U.S.A.*, 99(4):1882-1887 (2002).

Heitman et al., "Targets for Cell Cycle Arrest by the Immunosuppressant Rapamycin in Yeast," *Science*, 253:905-909 (1991).

Hershko and Ciechanover, "The Ubiquitin System," *Ann. Rev. Biochem.*, 67:425-479 (1998).

Ho et al., "Dimeric ligands define a role for transcription activation domains in reinitiation," *Nature*, 382(6594):822-826 (1996).

Houghten, "The Use of Synthetic Peptide Combinatorial Libraries for the Identification of Bioactive Peptides," *Biotechniques*, 13(3):412-421 (1992).

Jariel-Encontre et al., "Ubiquitinylation Is Not an Absolute Requirement for Degradation of c-Jun Protein by the 26 S Proteasome," *J. Biol. Chem.*, 270(19):11623-11627 (1995).

Jesenberger and Jentsch, "Deadly Encounter: Ubiquitin Meets Apoptosis," *Nat. Rev. Mol. Cell Biol.*, 3:112-121 (2002).

Kisselev et al., "The Sizes of Peptides Generated from Protein by Mammalian 26 and 20 S Proteasomes," *J. Biol. Chem.*, 274(6):3363-3371 (1999).

Köhler et al., "The Axial Channel of the Proteasome Core Particle Is Gated by the Rpt2 ATPase and Controls Both Substrate Entry and Product Release," *Mol. Cell*, 7:1143-1152 (2001).

Kopytek et al., "Chemically induced dimerization of dihydrofolate reductase by a homobifunctional dimer of methotrexate," *Chem. Biol.*, 7:313-321 (2000).

Lakso et al., "Targeted oncogene activation by site-specific recombination in transgenic mice," *Proc. Nat'l Acad. Sci. U.S.A.*, 89:6232-6236 (1992).

Lam, "A new type of synthetic peptide library for identifying ligand-binding activity," *Nature*, 354:82-84 (1991).

Lam, "Application of combinatorial library methods in cancer research and drug discovery," *Anti-Cancer Drug Des.*, 12:145-167 (1997).

Lam et al., "A proteasomal ATPase subunit recognizes the polybiqutin degradation signal," *Nature*, 416:763-767 (2002).

Leggett et al., "Multiple Associated Proteins Regulate Proteasome Structure and Function," *Mol. Cell*, 10:495-507 (2002).

Lee et al., "ATP-Dependent Proteases Degrade their Substrates by Processively Unraveling them from the Degradation Signal," *Mol. Cell.*, 7:627-637 (2001).

Li et al., "Targeted Mutation of the DNA Methyltransferase Gene Results in Embryonic Lethality," *Cell*, 69:915-926 (1992).

Liberles et al., "Inducible gene expression and protein translocation using nontoxic ligands identified by a mammalian three-hybrid screen," *Proc. Natl. Acad. Sci. U.S.A.*, 94:7825-7830 (1997).

Lin et al., "Dexamethasone-Methotrexate: an Efficient Chemical Inducer of Protein Dimerization *In Vivo*, " *J. Am. Chem. Soc.*, 122:4247-4248 (2000).

Lorenz and Heitman, "TOR Mutations Confer Rapamycin Resistance by Preventing Interaction with FKBP12-Rapamycin," *J. Biol. Chem.*, 270(46):27531-27537 (1995).

Matouschek, "Protein unfolding—an important process in vivo?" *Curr. Opin. Struct. Biol.*, 13:98-109 (2003).

Mueller and Feigon, "Structural determinants for the binding of ubiquitin-like domains to the proteasome," *Embo J.*, 22(18):4634-4645 (2003).

O'Gorman et al., "Recombinase-Mediated Gene Activation of Site-Specific Integration in Mammalian Cells," *Science*, 251(4999):1351-1355 (1991).

Palombella et al., "Role of the proteasome and NF-kB in streptococcal cell wall-induced polyarthritis," *Proc. Natl. Acad. Sci. U.S.A.*, 95:15671-15676 (1998).

Rivera et al., "A humanized system for pharmacologic control of gene expression," *Nat. Med.*, 2(9):1028-1032 (1996).

Sakamoto et al., "Protacs: Chimeric molecules that target proteins to the Skp1-Cullin-F box complex for ubiquitination and degradation," *Proc. Natl. Acad. Sci USA*, 98(15):8554-8559 (2001).

Sakamoto et al., "Development of Protacs to Target Cancer-Promoting Proteins for Ubiquitination and Degradation," *Mol. Cell Proteomics*, 2.12:1350-1358 (2003).

Scott and Smith, "Searching for Peptide Ligands with an Epitope Library," *Science*, 249:386-390 (1990).

Sikorski and Hieter, "A System of Shuttle Vectors and Yeast Host Strains Designed for Efficient Manipulation of DNA in *Saccharomyces cerevisiae*, " *Genetics*, 122:19-27 (1989).

Spencer et al., "Controlling Signal Transduction with Synthetic Ligands," *Science*, 262:1019-1024 (1993).

Strickland et al., "Recognition of Misfolding Proteins by PA700, the Regulatory Subcomplex of the 26 S Proteasome," *J. Biol. Chem.*, 275(8):5565-5572 (2000).

Tarcsa et al., "$Ca^{2+}$-free Calmodulin and Calmodulin Damaged by in Vitro Aging Are selectively Degraded by 26 S Proteasomes without Ubiquitination," *J. Biol. Chem.*, 275(27):20295-20301 (2000).

Thomas and Capecchi, "Site-Directed Mutagenesis by Gene Targeting in Mouse Embryo-Derived Stem Cells," *Cell*, 51:503-512 (1987).

Tofaris et al., "α-Synuclein metabolism and aggregation is linked to ubiquitin-independent degradation by the proteasome," *FEBS Lett.*, 509:22-26 (2001).

Wach et al., "Yeast Functional Analysis Reports: Heterologous *HIS3* Marker and GFP Reporter Modules for PCR-Targeting in *Saccharomyces cerevisiae*," *Yeast*, 13:1065-1075 (1997).

Whitby et al., "Structural basis for the activation of 20S proteasomes by 11S regulators," *Nature*, 408:115-120 (2000).

Wilmut et al., "Viable offspring derived from fetal and adult mammalian cells," *Nature*, 385:810-813 (1997).

Winston et al., "Construction of a Set of Convenient *Saccharomyces cerevisiae* Strains that are Isogenic to S288C," *Yeast*, 11:53-55 (1995).

Zhang et al., "Determinants of proteasome recognition of ornithine decarboxylase, a ubiquitin-independent substrate," *Embo. J.*, 22(7):1488-1496 (2003).

Zuckermann et al., "Discovery of Nanomolar Ligands for 7-Transmembrane G-Protein-Coupled Receptors from a Divers *N*-(Substituted)glycine Peptoid Library," *J. Med. Chem.* 37:2678-2685 (1994).

\* cited by examiner a

Rpn2-FPR1

Rpt5-FPR1

Pre10-FPR1

Rpn10-FPR1 b

TARGETED POLYPEPTIDE DEGRADATION

RELATED U.S. APPLICATION

This application claims priority to U.S. Provisional Patent Application No. 60/526,490 filed on Dec. 3, 2003, hereby incorporated by reference in its entirety for all purposes.

STATEMENT OF GOVERNMENT INTERESTS

This invention was made with government support under grant numbers DE-FG02-87ER-60565 from the Department of Energy and NIH U01HL066678 from the National Institutes of Health. The Government has certain rights in the invention.

BACKGROUND OF THE INVENTION

ATP-dependent protease complexes degrade many unstable cellular proteins. These molecular machines function both generally in protein turnover, and specifically in the regulation of processes such as transcription, apoptosis, antigen presentation and cell cycle progression (Jesenberger et al. (2002) *Nat. Rev. Mol. Cell Biol.* 3:112). A high degree of conservation is evident among them; the archaebacterial and eukaryotic 20S proteolytic core particles share both sequence and structural homology (Bochtler et al. (1999) *Ann. Rev. Biophys. Biomol. Struct.* 28:295), while eubacteria have functionally related complexes: ClpYQ, ClpXP and ClpAP (Bochtler et al. (2000) *Nature* 403:800; Bochtler et al. (1997) *Proc. Natl. Acad. Sci. U.S.A.* 94:6070; Groll et al. (1997) *Nature* 386:463). The 20S core particle (CP) is composed of four stacked heptameric rings structured in an $\alpha$-$\beta$-$\beta$-$\alpha$ configuration. Access to the proteolytic central chamber is obstructed at both ends of the cylindrical assembly by N-terminal projections of the $\alpha$-subunits, thus preventing uncontrolled proteolytic degradation (Groll et al. (1997) *Nature* 386:463; Whitby et al. (2000) *Nature* 408:115; Groll et al. (2000) *Nat. Struct. Biol.* 7:1062). In eukaryotes, docking with the 19S regulatory particle (RP) to form the complete 26S proteasome is sufficient to relieve this block, opening a channel into the core (Groll et al. (2000) *Nat. Struct. Biol.* 7:1062; Kohler et al. (2001) *Mol. Cell* 7:1143).

Eukaryotes have evolved an elaborate system that operates in conjunction with the proteasome to facilitate the temporal and specific regulation of intracellular proteolysis. Substrates targeted for degradation by the proteasome pathway are recognized by the E1, E2, and E3 ubiquitin conjugation machinery and tagged with polyubiquitin chains, which are thought to promote the proteolytic process through their binding with the proteasome. These three consecutively acting enzymes are necessary for target recognition, transfer of a ubiquitin moiety to the substrate, and subsequent elongation of the ubiquitin branched chain (Hershko et al. (1998) *Ann. Rev. Biochem.* 67:425). Modularity and the large number of E2 Ub-conjugating enzymes and E3 Ub-ligases allow for great specificity and flexibility in detecting a diverse range of substrates. Once a protein is polyubiquitinated, it can be recognized and degraded by the 26S proteasome.

The polyubiquitin chain is thought to play two possible roles. The first is to target the protein to the proteasome and the second is to initiate the process of degradation. The targeting hypothesis is supported by the identification of several proteasome subunits that either bind or crosslink to ubiquitin chains (Deveraux et al. (1994) *J. Biol. Chem.* 269:7059; Lam et al. (2002) *Nature* 416:763). Hypotheses for how ubiquitin-dependent initiation of degradation might occur include: allosteric regulation, channel opening, and assistance in the unfolding of the target (Groll et al. (2003) *Int. J. Biochem. Cell Biol.* 35:606).

SUMMARY OF THE INVENTION

The present invention is based in part on the discovery that polypeptide degradation by a proteasome can occur independently of ubiquitination of the polypeptide. Pursuant to this discovery, localization of a substrate to the proteasome is sufficient for degradation to occur. The present invention is further based on the discovery of compounds that can target a polypeptide for degradation by the proteasome by binding both the target polypeptide and the proteasome. It has been discovered that facilitating binding of a target polypeptide to the proteasome (via one or more small molecules that bind the proteasome and/or target polypeptide; dimerizing protein tags or modules; and the like) is sufficient to trigger proteasome-mediated degradation of the target polypeptide. Thus, a polypeptide may be selectively targeted for degradation by the proteasome by providing compounds that allow the binding of the target polypeptide to the proteasome. Accordingly, the present invention provides methods by which polypeptides may be localized to the proteasome and degraded independent of ubiquitin binding to the polypeptide. Such methods are useful for treating disorders associated with polypeptide (e.g., protein) expression and/or activity, as well as useful as research tools in the study of protein function, either alone or in the context of systems biology.

The present invention provides therapeutic methods and/or pharmaceutical compositions for treating disorders mediated by polypeptides by targeting these polypeptides for degradation. In one embodiment, the present invention provides a method and/or composition for therapeutic, targeted polypeptide degradation in a patient having a disorder associated with polypeptide expression and/or activity. In one aspect, one or more proteasome-localizing agents are administered to a patient having a disorder associated with polypeptide (e.g., protein) expression and/or activity. The proteasome-localizing agent binds both the polypeptide and the proteasome and allows degradation of the polypeptide by the proteasome. The resulting degradation of the polypeptide results in the reduction or alteration of one or more symptoms of the disorder. In one aspect, the proteasome-localizing agent is released from the proteasome to target another polypeptide for proteasome-mediated degradation.

The present invention also provides methods and/or compositions for selectively inactivating or activating pharmaceutical compounds. In one embodiment, the present invention provides a method and/or composition for inactivating a pharmaceutical compound (e.g., a therapeutic polypeptide) in a patient when the pharmaceutical compound is no longer needed by targeting the pharmaceutical compound for degradation by the proteasome. In one aspect, one or more proteasome-localizing agents are administered to the patient. A proteasome-localizing agent binds both the pharmaceutical compound and the proteasome, and allows degradation of the pharmaceutical compound by the proteasome, resulting in inactivation of the pharmaceutical compound. In another embodiment, the present invention provides a method and/or composition for activating a pharmaceutical compound. In one aspect, the pharmaceutical compound in a patient is associated with a target polypeptide and rendered inactive. A proteasome-localizing agent may be administered to the patient when activation of the therapeutic activity of the pharmaceutical compound is desired. In one aspect, one or more proteasome-localizing agents are administered to the patient to bind both the target polypeptide associated with the pharmaceutical compound and the proteasome, thus allowing degradation of the target polypeptide by the proteasome. After degradation of the target polypeptide, the pharmaceutical compound is released from the proteasome in a therapeutically active form.

The present invention also provides tools and/or models for identifying compounds that mediate proteasome localization and/or polypeptide degradation. In one aspect, compounds that mediate proteasome localization and/or polypeptide degradation are identified by assaying the ability of these compounds to mediate one or more activities associated with proteasome-mediated polypeptide degradation including, but not limited to: binding a proteasome; binding a polypeptide; binding a proteasome-localizing agent; binding a proteasome-localizing agent module; binding a polypeptide and a proteasome; and allowing proteasome-mediated degradation of a polypeptide independent of polypeptide ubiquitination. Accordingly, another embodiment of the present invention is directed to methods of screening compounds useful for directing one or more of these activities using the screening assays described herein. In yet another embodiment, the present invention is directed to methods of using the tools and models described herein to study protein function, either alone or in the context of systems biology. In certain aspects, compounds are screened in vitro using the cell free assays described herein. In other aspects compounds are screened in vivo using the cells and/or organisms described herein.

The present invention further provides cells and/or organisms expressing one or more altered proteasome subunits expressing a proteasome-localizing agent or a portion thereof (e.g., a first module that interacts with a second module). In certain embodiments, the cell and/or organism expresses a polypeptide that is associated with a proteasome-localizing agent or a portion thereof (e.g., a second module that interacts with a first module). In other embodiments, the cell and/or organism expresses both one or more altered proteasome subunits associated with a proteasome-localizing agent or a module thereof and a polypeptide associated with a proteasome-localizing agent or a module thereof. In certain aspects, a compound that increases or decreases the ability of two or more modules to interact with one another (e.g., dimerize) may be administered to the cell and/or organism to increase or decrease polypeptide degradation by the proteasome. In one aspect, a cell is a eukaryotic cell such as *Saccharomyces cerevisiae*. In another aspect, the organism is a transgenic animal such as a mouse.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION

Figure 1:
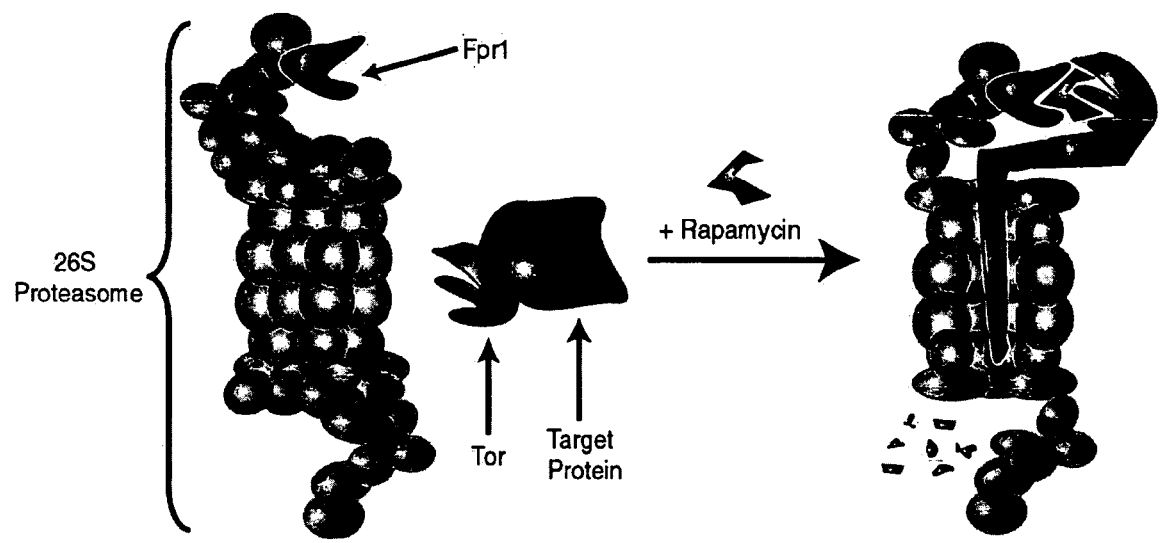
FIG. 1 depicts a schematic of the experimental design for testing whether localization to the proteasome is sufficient for degradation. One module of the heterodimerizing pair (Fpr1) is fused to the proteasome subunit. The other module (Tor) is fused to a reporter protein. Heterodimerization of the modules occurs upon addition of the small molecule rapamycin. This brings the reporter protein into close proximity to the proteasome.

Embodiments of the present invention are directed to the discovery that localizing a protein to the proteasome independent of polyubiquitin chain addition results in protein degradation by the proteasome. Accordingly, the present invention provides the use of proteasome-localizing agents (e.g., small molecules, heterodimerizing modules and the like) that can localize polypeptides to the proteasome in order to promote their degradation. As used herein, the terms "protein degradation" and "polypeptide degradation" include, but are not limited to, cleavage of a protein or polypeptide, respectively, into fragments or peptide substituents. Protein degradation can be mediated by one or more subunits of a proteasome. As used herein, the term "polypeptide" is intended to include, but is not limited to, peptides that are ten or 100 or more amino acids in length, as well as proteins and portions of proteins.

Therapeutic Methods

The present invention provides a novel approach to protein therapeutics using targeted protein and/or targeted polypeptide degradation. As used herein, the terms "targeted protein degradation" and "targeted polypeptide degradation" are intended to include, but are not limited to, targeting proteins or polypeptides, respectively to the proteasome for degradation. The current paradigm in screening small molecule libraries is to find inhibitors of enzymatic processes that are causal in disease. However, the number of small molecules that both specifically bind to, and inhibit the function of a polypeptide (i.e., via inhibiting one or more active sites) is extremely small. Furthermore, as active sites tend to be highly conserved or convergent, compounds that inhibit the active site of a targeted protein and/or polypeptide may also exhibit undesirable cross-reactivity with active sites of one or more non-targeted proteins and/or polypeptides. Compounds that target proteins and/or polypeptides to the proteasome could help limit the degree of this kind of cross-reactivity.

Targeted protein and/or polypeptide degradation is also useful for developing catalytic therapeutic agents. For example, a therapeutic agent of the present invention targets a specific polypeptide to the proteasome for degradation. After degradation, the agent is released and available to target another polypeptide to the proteasome for degradation. This could allow for lower doses of the agent to be used therapeutically, resulting in lower costs and less side effects.

The present invention also provides methods and compositions for modulating (i.e., increasing or decreasing) one or more activities of the polypeptides, compounds and/or proteasome-localizing agents described herein. In one aspect, the present invention provides methods and compositions for controlling selective degradation of therapeutic polypeptides (e.g., protein-based therapeutic compositions) when they are no longer needed for therapy, and for activating therapeutic compounds via proteasome-mediated degradation.

Accordingly, in one embodiment, a modulatory method of the invention involves contacting a cell with an agent that promotes targeting to the proteasome and/or promotes polypeptide degradation. Methods of modulating targeting to the proteasome and/or polypeptide degradation can be performed in vitro (e.g., by culturing a cell with the agent or using a cell-free proteasome assay) or, alternatively, in vivo (e.g., by administering the agent to a subject, such as a transgenic animal described herein). As such, the present invention provides methods of treating an individual afflicted with a polypeptide-associated disease or disorder. In one embodiment, the method involves administering an agent (e.g., an agent identified by a screening assay described herein), or combination of agents that promotes targeting to the proteasome and/or polypeptide degradation.

Another embodiment of the present invention is directed to a method for treatment of a disease or disorder associated with the expression and/or activity of one or more polypeptides which includes the step of administering a therapeutically effective amount of an agent which increases degradation of the polypeptide(s) and/or targeting to the proteasome. As defined herein, a therapeutically effective amount of agent (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an agent can include a single treatment or, preferably, can include a series of treatments. It will also be appreciated that the effective dosage of in used for treatment may increase or decrease over the course of a particular treatment. Changes in dosage may result from the results of diagnostic assays as described herein.

As used herein, a disorder associated with the expression and/or activity of a polypeptide (i.e., "a polypeptide-associated disorder") includes a disorder, disease or condition which is caused or characterized by a misregulation (e.g., upregulation) of a polypeptide. Polypeptide-associated disorders can detrimentally affect cellular functions including, but not limited to, cellular proliferation, growth, differentiation, or migration, inter- or intra-cellular communication, tissue function, systemic responses in an organism, susceptibility to pathogenic infections, immune responses, and protection of cells from toxic compounds (e.g., carcinogens, toxins, or mutagens).

In at least certain examples, the proteasome-localizing agents disclosed herein can be used in the treatment of polypeptide-associated disorders such as cellular proliferative disorders, (e.g., cancer). Treatment of cellular proliferative disorders is intended to include inhibition of proliferation including rapid proliferation. As used herein, the term "cellular proliferative disorder" includes disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995)). The terms "neoplasm" and "tumor" refer to an abnormal tissue that grows by cellular proliferation more rapidly than normal and continues to grow after the stimuli that initiated proliferation is removed (see, for example, PDR Medical Dictionary 1st edition (1995)). Such abnormal tissue shows partial or complete lack of structural organization and functional coordination with the normal tissue which may be either benign (i.e., benign tumor) or malignant (i.e., malignant tumor).

The language "treatment of cellular proliferative disorders" is intended to include the prevention of the growth of neoplasms in a subject or a reduction in the growth of pre-existing neoplasms in a subject. The inhibition also can be the inhibition of the metastasis of a neoplasm from one site to another. Examples of the types of neoplasms intended to be encompassed by the present invention include but are not limited to those neoplasms associated with cancers of the breast, skin, bone, prostate, ovaries, uterus, cervix, liver, lung, brain, larynx, gallbladder, pancreas, rectum, parathyroid, thyroid, adrenal gland, immune system, neural tissue, head and neck, colon, stomach, bronchi, and/or kidneys.

Cellular proliferative disorders can further include disorders associated with hyperproliferation of vascular smooth muscle cells such as proliferative cardiovascular disorders, e.g., atherosclerosis and restinosis. Cellular proliferation disorders can also include disorders such as proliferative skin disorders, e.g., X-linked ichthyosis, psoriasis, atopic dermatitis, allergic contact dermatitis, epidermolytic hyperkeratosis, and seborrheic dermatitis. Cellular proliferative disorders can further include disorders such as autosomal dominant polycystic kidney disease (ADPKD), mastocystosis, and cellular proliferation disorders caused by infectious agents such as viruses.

In at least certain examples, the proteasome-localizing agents disclosed herein can be used in the treatment of disorders associated with pathogen infection. Disorders associated with infection by pathogens include, but are not limited to, infection by viruses (DNA viruses, RNA viruses, animal viruses, and the like), bacteria (e.g., gram positive bacteria, gram negative bacteria, acid-fast bacteria, and the like), fungi, parasitic microbes and the like.

Proteasome-localizing agents disclosed herein are also useful for treating disorders associated with aberrant peptide folding and/or aberrant peptide degradation. Such disorders include, but are not limited to, cellular proliferation disorders, prion diseases (e.g., scrapie, Creutzfeldt-Jakob disease, Gerstmann-Strassler Scheinker disease, bovine spongiform encephalopathy and the like) Alzheimer's disease, Parkinson's disease, Huntington's disease, type II diabetes, cystic fibrosis, emphysema, spinocerebellar ataxia, $\alpha$-1-antitrypsin deficiency, and the like.

Pharmaceutical Compositions

Agents and/or compounds that affect proteasome targeting and/or polypeptide degradation (e.g., modulating agents such as proteasome-localizing agents) can be incorporated into pharmaceutical compositions suitable for administration. Such compositions typically comprise the modulatory agent(s) and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Screening Assays

The invention provides a method (also referred to herein as a "screening assay") for identifying modulators of proteasome targeting and/or polypeptide degradation, i.e., candidate or test compounds or agents (e.g., peptides, cyclic peptides, peptidomimetics, small molecules, small organic molecules, or other drugs) which promote targeting to the proteasome and/or the degradation of a target polypeptide (e.g., polypeptides that contribute to disease, therapeutic polypeptides and the like). Candidate or test compounds or agents that promote targeting to the proteasome and/or degradation of a polypeptide include, but are not limited to, proteasome-localizing agents. Proteasome-localizing agents may comprise two or more modules that interact (e.g., modules that form dimers, trimers, tetramers and the like) to target a polypeptide to a proteasome, or may comprise individual agents or compounds that target a polypeptide to a proteasome.

As used herein, the terms "bind," "binding," "interact," "interacting," "associated with" are intended to include, but are not limited to, covalent and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions are much weaker than covalent interactions, but play a major role in determining the three-dimensional structure of macromolecular structures. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

As used herein, the term "small organic molecule" refers to an organic molecule, either naturally occurring or synthetic, that has a molecular weight of more than about 25 daltons and less than about 3000 daltons, preferably less than about 2500 daltons, more preferably less than about 2000 daltons, preferably between about 100 to about 1000 daltons, more preferably between about 200 to about 500 daltons.

In one embodiment, the invention provides assays for screening candidate or test compounds which modulate polypeptide degradation via the proteasome. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412), or on beads (Lam (1991) *Nature* 354:82), chips (Fodor (1993) *Nature* 364:555), bacteria (Ladner U.S. Pat. No. 5,223,409), spores (Ladner U.S. Pat. No. 5,223,409), plasmids (Cull et al. (1992) *Proc. Natl. Acad. Sci. USA* 89:1865) or on phage (Scott and Smith (1990) *Science* 249:386); (Devlin (1990) *Science* 249:404); (Cwirla et al. (1990) *Proc. Natl. Acad. Sci. USA* 87:6378); (Felici (1991) *J. Mol. Biol.* 222:301); (Ladner supra).

In one embodiment, test compounds of the invention (e.g., proteasome-localizing agents) include dimerizing modules comprising a first module and a second module that bind to one another to form a dimeric (e.g., heterodimeric) compound. In one aspect, a first module binds a polypeptide to be targeted to the proteasome and second module binds the proteasome. Upon binding of the first and second modules to form a dimeric (e.g., heterodimeric) compound, the targeted polypeptide is degraded by the proteasome. Examples of modules that bind to proteasomes include, but are not limited to: proteasome binding molecules that do not inhibit the proteasome; analogs of the Ubiquitin/Ubl helix motif that bind to the proteasome (Mueller et al. (2003) *EMBO J.* 22:4634); and the like.

In one embodiment, modules are screened separately. A module that binds a proteasome can be chemically crosslinked to a module that binds a target polypeptide to form a heterodimeric compound that localizes the target polypeptide to the proteasome. In one aspect of the invention, crosslinking compounds can be used to increase the screening efficiency by increasing the effective search space for small molecule dimerizers by the square of the size of the library, which for a 10,000 member screen, is approximately $1 \times 10^5$-fold. Crosslinkers are well known in the art and are commercially available from companies such as Pierce Biotechnology, Inc. (Rockford, Ill.).

Certain embodiments of the present invention provide organism-based screening assays. In one embodiment, an organism-based assay provides an organism for screening compounds that target polypeptides to the proteasome for degradation to identify novel therapeutic compounds. Useful organisms include yeast such as *Saccharomyces cerevisiae*, and mammals such as non-human primates, rabbits, rats, mice, and the like and transgenic species thereof. Polypeptide degradation can be assayed using a variety of techniques known to those of skill in the art.

In another embodiment, an organism-based screening assay provides an organism that expresses one or more target proteins and/or polypeptides expressing a tag that binds to a proteasome. In one aspect, the tag (i.e., an epitope tag such as hemagglutinin (HA), c-myc or TAP) does not directly bind the proteasome but is instead conjugated to a compound (e.g., a small molecule or a heterodimerizer) that binds the proteasome. Alternatively, compounds that bind both to the tag and the proteasome can be used. In another aspect, the target protein and/or polypeptide is bound to a monoclonal antibody conjugated to a compound that binds a proteasome. In one aspect of the invention, this assay is useful for designing modulated compounds or tags (i.e., increasing or decreasing the ability of the compound or tag to direct protein and/or polypeptide degradation and/or changing the protein and/or polypeptide binding specificity of the compound or tag).

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. U.S.A.* 89:6232. Another example of a recombinase system is the FLP recombinase system of *S. cerevisiae* (O'Gorman et al. (1991) *Science* 251:1351). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

The present invention also provides cell-based screening assays for screening compounds that target polypeptides to the proteasome for degradation to identify novel therapeutic compounds. In one aspect, a cell for use in a cell-based screening assay can be derived from the animal models described herein. In one aspect, cells of the present invention are eukaryotic cells such as *S. cerevisiae* cells, insect cells, *Xenopus* cells, or mammalian cells (such as Chinese hamster ovary cells (CHO), African green monkey kidney cells (COS), fetal human cells (293T) and the like). Other suitable host cells are known to those skilled in the art.

The present invention further provides cell-free assays in which a proteasome and a target protein, polypeptide or biologically active portion thereof, is contacted with a test compound, and the ability of the test compound to modulate proteasome binding and/or degradation of the target protein, polypeptide or biologically active portion thereof, is determined.

This invention further pertains to novel agents identified by the above-described screening assays. Accordingly, it is within the scope of this invention to further use an agent identified as described herein in an appropriate animal model as described herein. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments of disorders associated with protein and/or polypeptide expression.

Functional Assays

The present invention further provides systems for elucidating polypeptide function. In one embodiment, the assays and compounds described herein are used to target a specific polypeptide in a cell or in an organism to the proteasome for degradation. The function(s) of the protein and/or polypeptide may then be determined by assaying responses of the cell or the organism to the absence of the polypeptide. The assays described herein are advantageous over many knockout systems known in the art because they allow a high degree of regulation. For example, the target polypeptide may be degraded at various time points during development. The target polypeptide may also be degraded to various degrees ranging from 100% of the polypeptide degraded, to 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, 5% or less of the polypeptide degraded. Multiple polypeptides may also be degraded in a single cell or organism at the same time or at various time points. Multiple polypeptides may further be degraded in a single cell or organism to various degrees relative to one another.

In one embodiment, the present invention provides organism-based assays for determining the function of a polypeptide in vivo. In one aspect, the invention provides an organism that expresses a proteasome fused to a first module (i.e., a first portion of a dimerizing module), and a target protein and/or polypeptide fused to a second module (i.e., a second portion of a dimerizing module), wherein the first and second modules interact upon exposure to a particular compound (i.e., a heterodimerizer) to form a dimeric module. In another aspect, the first and second modules may interact to form a dimer without exposure to a particular compound (i.e., a heterodimerizer). Module-module interactions can direct localization of the target polypeptide to a proteasome as well as the proteasome-mediated degradation of the target polypeptide. In another embodiment, only the proteasome or the target polypeptide is fused to a module. In one aspect, the organism-based assays and/or compounds described herein can be used to mediate targeted polypeptide degradation to determine the function of a polypeptide in vivo.

Examples of heterodimerizers include, but are not limited to: FK-506 (Ho et al. (1996) *Nature* 382:822); FK-506-cyclosporin A (Belshaw et al. (1996) *Proc. Natl. Acad. Sci. USA* 93:4604); aptamers (Colas et al. (2000) *Proc. Natl. Acad. Sci. USA* 97:13720); coumermycin (Farrar et al. (1996) *Nature* 383:178); bismethotrexate (2000) *Chem. and Biol.* 7:313); dexamethasone-methotrexate (Lin et al. (2000) *J. Am. Chem. Soc.* 122:4247); RNA-protein binder (Harvey et al. (2002) *Proc. Natl. Acad. Sci. U.S.A.* 99:1882); rapamycin derivatives (Liberles et al. (1997) *Proc. Natl. Acad. Sci. U.S.A.* 94:7825); and the like. These references are incorporated herein by reference in their entirety.

Animals and Cells

Assays described herein (e.g., screening assays) may be carried out using non-human transgenic animals. For example, in one embodiment, a host cell of the invention is a fertilized oocyte or an embryonic stem cell into which a modified proteasome sequence and/or proteasome-targeted protein or polypeptide has been introduced. Such host cells can then be used to create non-human transgenic animals in which exogenous proteasome, protein and/or polypeptide sequences have been introduced into their genome. Such animals are useful for studying proteasome targeting and for identifying and/or evaluating compounds that target polypeptides and/or proteins to the proteasome. As used herein, a "transgenic animal" is a non-human animal, e.g., a mammal such as a rodent, for example, a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, e.g., a mammal such as a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a nucleic acid (i.e., a transgene) encoding a proteasome or a portion thereof, a protein of interest or a polypeptide of interest into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to a detectable translation product transgene to direct expression of a detectable translation product to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al., and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of a detectable translation product transgene in its genome and/or expression of detectable translation product mRNA in tissues or cells of the animals. A transgenic founder animal can then be used to breed additional animals carrying the transgene. Moreover, transgenic animals carrying a transgene encoding a detectable translation product can further be bred to other transgenic animals carrying other transgenes.

To create a homologous recombinant animal, a vector is prepared which contains at least a portion of a transgene. In one embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid sequence of the gene to allow for homologous recombination to occur between the exogenous gene carried by the vector and an endogenous gene in an embryonic stem cell. The additional flanking nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stem cell line (e.g., by electroporation) and cells in which the introduced gene has homologously recombined with the endogenous gene are selected (see e.g., Li, E. et al. (1992) Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) Current Opinion in Biotechnology 2:823 and in PCT International Publication Nos.: WO 90/11354 by Le Mouellec et al.; WO 91/01140 by Smithies et al.; WO 92/0968 by Zijlstra et al.; and WO 93/04169 by Berns et al.

Clones of the non-human transgenic animals described herein can also be produced according to the methods described in Wilmut, I. et al. (1997) Nature 385:810. In brief, a cell, e.g., a somatic cell, from the transgenic animal can be isolated and induced to exit the growth cycle and enter $G_0$ phase. Alternatively, a cell, e.g., an embryonic stem cell, from the inner cell mass of a developing embryo can be transformed with a preferred transgene. Alternatively, a cell, e.g., a somatic cell, from cell culture line can be transformed with a preferred transgene and induced to exit the growth cycle and enter $G_0$ phase. The cell can then be fused, e.g., through the use of electrical pulses, to an enucleated mammalian oocyte. The reconstructed oocyte is then cultured such that it develops to morula or blastocyst and then transferred to pseudopregnant female foster animal. The offspring borne of this female foster animal will be a clone of the animal from which the nuclear donor cell, e.g., the somatic cell, is isolated.

Vector DNA can be introduced into cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Selectable markers include those which confer resistance to drugs, such as G418, hygromycin and methotrexate. Nucleic acid encoding a selectable marker can be introduced into a host cell on the same vector as that encoding a detectable translation product or can be introduced on a separate vector. Cells stably transfected with the introduced nucleic acid can be identified by drug selection (e.g., cells that have incorporated the selectable marker gene will survive, while the other cells die).

The following examples are provided for exemplification purposes only and are not intended to limit the scope of the invention that has been described in broad terms above.

EXAMPLE I

Proteasome Degradation System

Chemical inducers of dimerization are a class of reagents that facilitate the regulated association of any two polypeptides. They have been used in a number of applications such as localization of proteins to subcellular domains, triggering of signal transduction cascades, and control of gene expression (Kopytek et al. (2000) Chem. Biol. 7:313; Spencer et al. (1993) Science 262:1019; Ho et al. (1996) Nature 382:822; Farrar et al. (1996) Nature 383:178; Belshaw et al. (1996) Proc. Natl. Acad. Sci. U.S.A. 93:4604; Rivera et al. (1996) Nat. Med. 2:1028). To determine whether localization to the proteasome was sufficient for degradation, such a system was modified and utilized in S. cerevisiae. A first heterodimerizing module was fused to the proteasome, and a second heterodimerizing module was fused to the reporter to be tested for degradation. Addition of a chemical dimerizer brought the two modules together, thus localizing the reporter to the site of the proteasome. Degradation occurred as a result of the drug-induced association could be monitored with the appropriate assay (FIG. 1).

Figure 2:
FIGS. 2A-2B depict fusion constructs. (A) depicts the heterodimerizing module FPR1 genomically fused immediately downstream of each of the seven proteasome subunits in the strain DY001. Four of the derivative strains were viable. (B) depicts reporter proteins having an N-terminal fusion of the heterodimerizing module Tor to the selective marker His3. The non-heterodimerizing control reporter has an S1972R mutation in Tor that disrupts binding to the Fpr1-rapamycin complex.
Figure 2:
Figure 2:
Figure 3:
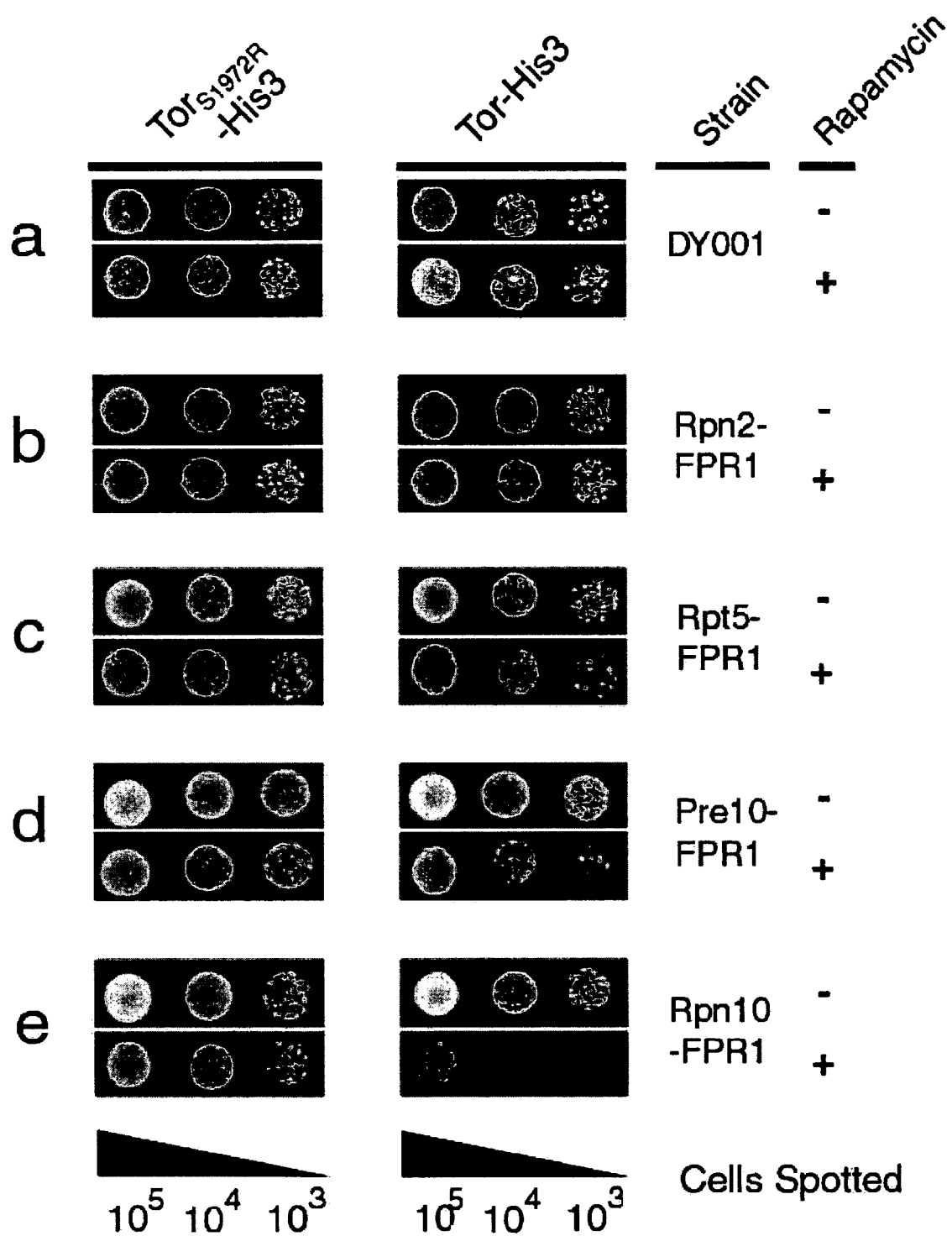
FIGS. 3A-3E depict a screen for Fpr1-tagged proteasome strains that exhibit growth deficient phenotypes. (A) illustrates that the DY001 control strain grows equally well when expressing either Tor-His3 or $Tor_{S1972R}$-His3 in the presence or absence of rapamycin. (B) and (C) illustrate that strains Rpn2-FPR1 and Rpt5-FPR1 show little or no difference in growth in the presence or absence of rapamycin. (D) and (E) illustrate that strains Pre10-FPR1 and Rpn10-FPR1 show decreased growth when expressing Tor-His3, and spotted growth on media containing rapamycin.

In *S. cerevisiae*, the lipophilic macrolide rapamycin has been shown to bind with high affinity to the protein Fpr1, and this complex in turn binds to the ligand-binding domain of Tor1 (Tor1$^{1883-2078}$, or hereafter Tor) (Lorenz et al. (1995) *J. Biol. Chem.* 270:27531). Seven proteasome subunits (Rpn2, Rpt2, Rpt5, Rpn6 Pre10, Rpn10, Rpn11) that ranged in distance from the 20S proteolytic core were each C-terminally fused with Fpr1 (FIG. 2A). Strains bearing FPR1-tagged Rpt2, Rpn6 and Rpn11 subunits could not be recovered, which, without intending to be bound by theory, was due to their lethality. DY001 strains expressing Rpn2, Rpt5, Pre10 and Rpn10 FPR1-tagged subunits (henceforth referred to as strain subunit-FPR1) were viable, contained correct integrated fragments as determined by PCR, and exhibited wild-type expression levels as determined by Western blotting.

EXAMPLE II

Screen for Growth Deficient Phenotypes

A gradient growth assay was used to screen the viable strains containing Fpr1-tagged proteasome subunits to identify degradation-through-localization (DTL) candidates. The auxotrophic marker HIS3 encodes a protein involved in histidine biosynthesis, and is necessary for growth on histidine-dropout media. Each Fpr1-tagged strain used in this assay had its chromosomal copy of HIS3 deleted and, therefore, required expression of exogenous functional His3 for growth. Two reporter constructs were designed for use in the screen. The reporter Tor-His3 is an amino-terminal fusion of the heterodimerizing module Tor with full length His3 (FIG. 2B). The control reporter $Tor_{S1972R}$-His3 replaced wild-type Tor with a missense mutant protein that has a decreased affinity for the rapamycin-Fpr1 complex (Heitman et al. (1991) *Science* 253:905).

Identification of DTL candidates was based on the comparative growth of strains on histidine-dropout solid media, with or without rapamycin. Fpr1-tagged strains that expressed the control reporter $Tor_{S1972R}$-His3 were not expected to show any difference in growth between the two plates; the fusion protein would not bind rapamycin and therefore should not be directed to the proteasome. Tor-His3 binds rapamycin and, therefore, can have an increased association with the proteasome in the presence of the drug. Without intending to be bound by theory, if this association were sufficient for degradation, Tor-His3 containing strains would be expected to display a growth deficient phenotype on the histidine-dropout plates with rapamycin.

The untagged DY001 parental and the four viable Fpr1-tagged strains were individually transformed with the experimental and control reporter constructs. All strains grew equally well on control plates containing histidine. Each transformant was then spotted as a 10-fold dilution series ($10^3$-$10^5$) on two sets of experimental plates: histidine-dropout media either containing or lacking rapamycin (FIGS. 3A-3E). Strain Rpn10-FPR1 displayed the most striking rapamycin-dependent phenotype. Strain Pre10-FPR1 had a milder growth deficient phenotype that was still significant and reproducible. Strains Rpn2-FPR1 and Rpt5-FPR1 did not show comparative growth phenotypes consistent with degradation of the reporter constructs.

EXAMPLE III

Western Assays Confirm DTL

Figure 4:
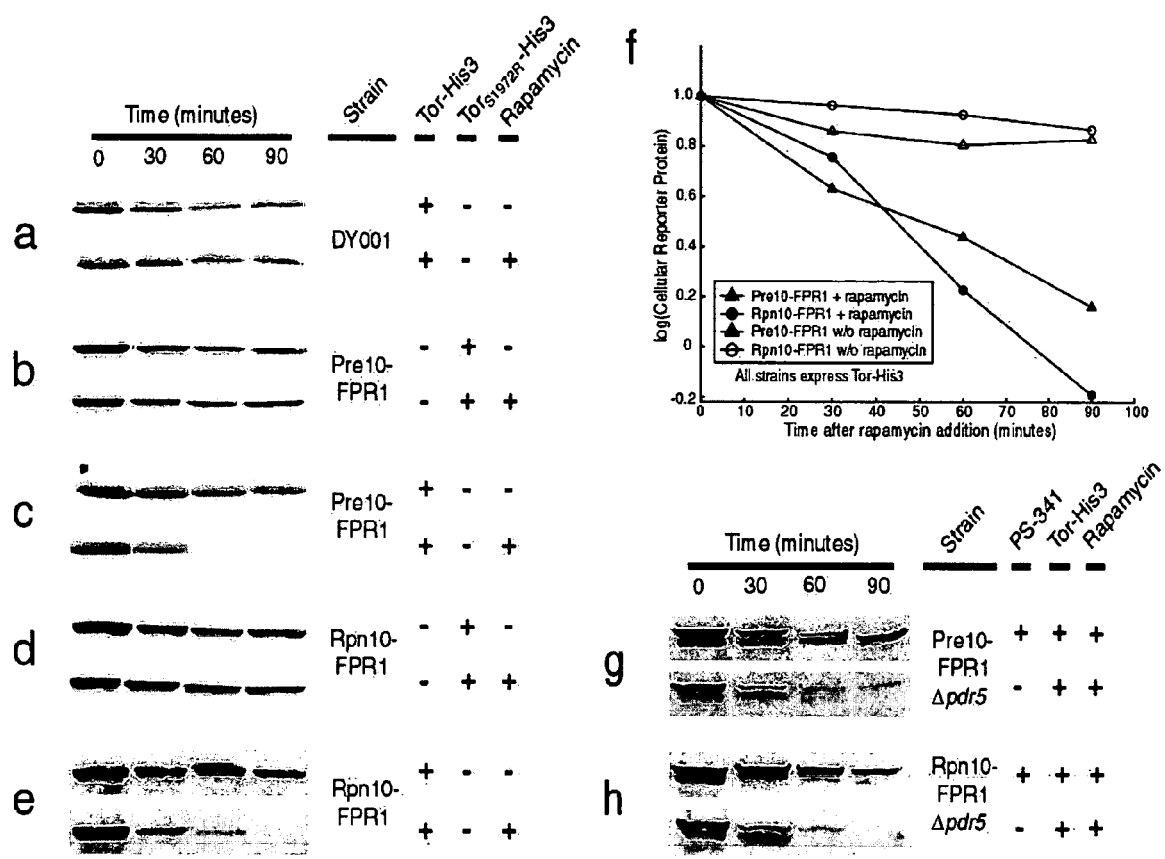
FIGS. 4A-4H depict Tor-His3 degradation in vivo in the presence of rapamycin. (A) depicts a 90 minute time course in which untagged strains grown in culture demonstrate no difference in degradation rates in the presence or absence of rapamycin. (B) and (D) demonstrate that control reporter fusions in strains Pre10-FPR1 and Rpn10-FPR1 show no difference in the rate of degradation in the presence or absence of rapamycin. C and E show that Tor-His3 expressed either in strain Pre10-FPR1 or strain Rpn10-FPR1 was rapidly degraded in the presence of rapamycin. (F) graphically depicts Tor-His3 degradation in the presence or absence of rapamycin in strains Pre10-FPR1 and Rpn10-FPR1. (G) and (H) show that addition of the proteasome inhibitor PS-341 prevented Tor-His3 from degrading in strain Pre10-FPR1 (G) and Rpn10-FPR1 (H), even in the presence of rapamycin. PDR5 encodes a multi-drug resistance transporter that was knocked-out in strains Pre10-FPR1 and Rpn10-FPR1 for the purpose of the PS-341 experiments.

The aforementioned growth assay was a convenient tool for isolating strains to further explore DTL. Use of the growth assay on its own did not prove that localization was sufficient for degradation since His3 function could have been compromised in a rapamycin-dependent, but degradation-independent manner. To address this point, degradation of the reporters was directly measured. Strains Pre10-FPR1 and Rpn10-FPR1 were singly transformed with plasmids that expressed hemagglutinin (HA) epitope-tagged versions of Tor-His3 and $Tor_{S1972R}$-His3. The transformants were grown in liquid culture to early log phase, whereupon cycloheximide was added to halt protein translation. Each culture was then split in two and rapamycin was added to one. Samples were collected at various times and whole-cell protein extracts were generated and used for Western analysis (FIGS. 4A-4H). Both strains Pre10-FPR1 and Rpn10-FPR1 displayed an increase in the rate of degradation of the reporter Tor-His3 when rapamycin was added to the cultures, with half-lives of approximately 20-30 minutes (FIG. 4B). No difference in the rate of degradation was observed with Fpr1-tagged strains expressing the mutant reporter $Tor_{S1972R}$-His3. To demonstrate that degradation of the reporter was mediated by the proteasome and not processed through other pathways, the experiments were repeated with the addition of the proteasome inhibitor PS-341 (FIG. 4C) (Palombella et al. (1998) *Proc. Natl. Acad. Sci. U.S.A.* 95:15671). As expected, addition of PS-341 halted degradation of Tor-His3, even in the presence of rapamycin. These experiments confirm that the growth deficient phenotype seen on histidine-dropout media was due to the degradation of the Tor-His3 reporter and that the 26S proteasome is necessary for this to occur.

EXAMPLE IV

Purified Proteasomes are Sufficient for DTL

Figure 5:
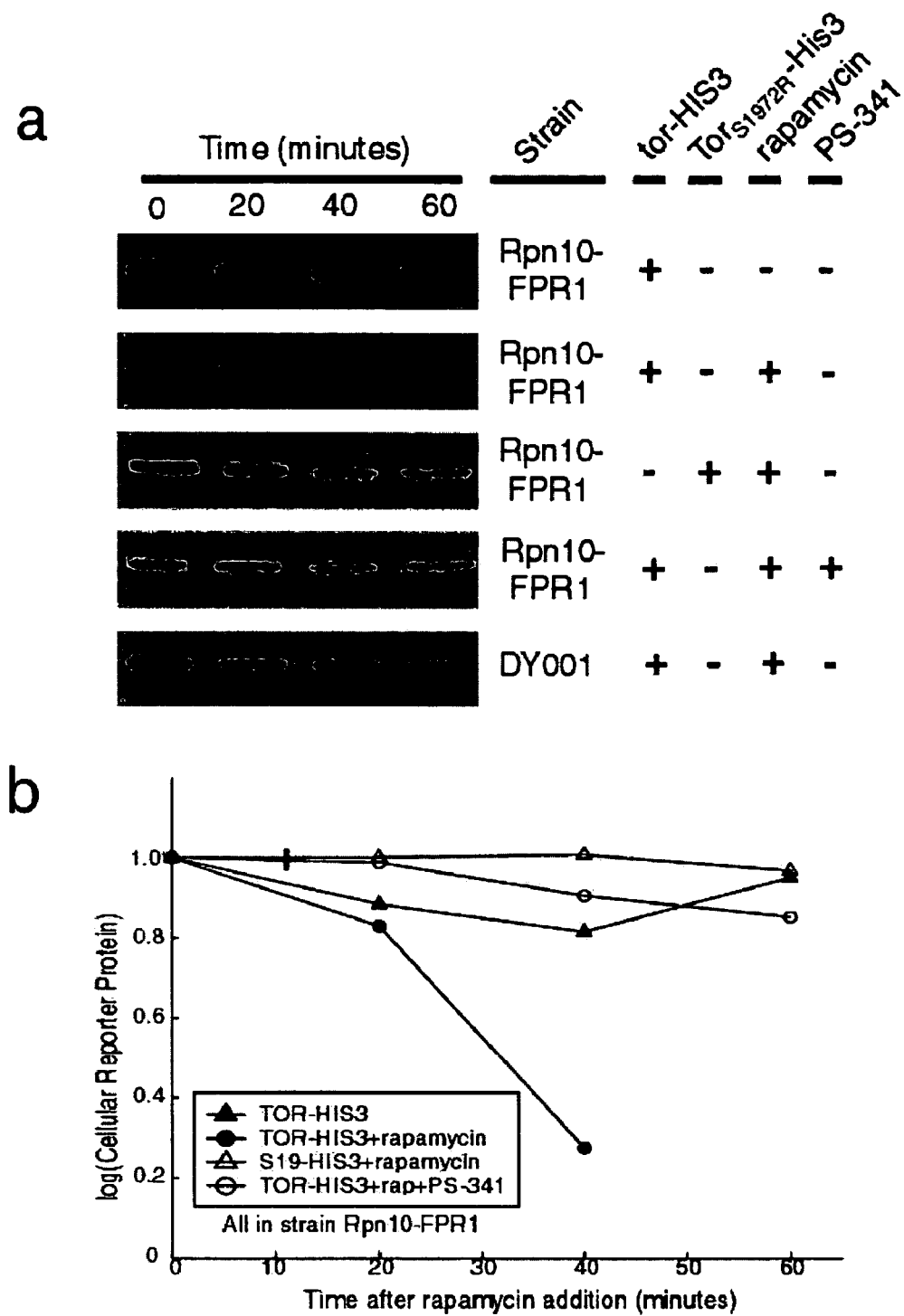
FIGS. 5A-5B depict Tor-His3 degradation in vitro in the presence of rapamycin. (A) depicts a 60 minute time course that demonstrates the rapid degradation of purified Tor-His3 when mixed with Rpn10-FPR1-tagged, purified proteasome complexes in the presence of rapamycin. There was no appreciable degradation of the reporter using the mutant construct, untagged proteasome, tagged proteasome in the absence of rapamycin, or tagged proteasome in the presence of rapamycin and a proteasome inhibitor. (B) graphically depicts Tor-His3 degradation in the presence or absence of rapamycin in experiments containing purified Rpn10-FPR1 proteasomes. $Tor_{S1972R}$-His3 is labeled as S19-HIS3.

To demonstrate ubiquitin-independence and that the 26S proteasome is not only necessary but also sufficient for DTL, in vitro experiments were performed where the only degradation components used were purified proteasomes and reporter proteins. Whole, functional 26S proteasomes have been previously affinity-purified for use in biochemical assays (Leggett et al. (2002) *Mol. Cell* 10:495). The same procedure was used to isolate proteasomes from strain Rpn10-FPR1. HA epitope-tagged versions of Tor-His3 and $Tor_{S1972R}$-His3 were purified from a bacterial expression system and then mixed with the proteasomes, with or without rapamycin. Samples were extracted at regular intervals and reporter degradation was monitored by Western analysis (FIG. 5A). The in vitro results mirrored what was seen with the in vivo Westerns blots. All experiments using purified $Tor_{S1972R}$-His3 demonstrated no degradation. Degradation of Tor-His3 was only observed in the presence of rapamycin and proteasomes isolated from strain Rpn10-FPR1. The half-life of the reporter was on the order of 15 minutes (FIG. 5B), comparable to that which was observed in vivo. Once again, proteolysis of Tor-His3 could be halted upon the addition of the proteasome inhibitor PS-341. These results, in combination with the in vivo experiments, demonstrate that localization to the proteasome is sufficient for the initiation of degradation.

EXAMPLE V

Conditional Protein Knockdown

The system presented herein will be converted into a generalized method for the facile construction of conditional protein knockdowns in *S. cerevisiae*. Fusing the Tor module to endogenous proteins of choice in an Rpn10-FPR1 background will permit rapamycin-dependent control of degradation. The estimated 20-30 minutes half-lives of the target proteins will compare favorably with established high-throughput knockdown methods such as RNA interference and promoter shutoff assays (Fire et al. (1988) *Nature* 391:806; Baron et al. (2000) *Methods Enzymol.* 327:401). One advantage of the present system over both technologies is that the system described herein will directly target proteins and/or polypeptides for degradation, whereas the other systems affect RNA levels and are therefore dependent on the targets' natural half-lives for functional knockdowns.

EXAMPLE VI

Murine Model

A mouse model will be used to develop an adaptor molecule that is capable of binding to the proteasome in mammalian systems as well as a protein and/or peptide of interest. This molecule will thus target the peptide and/or protein for degradation without the need for modification of the proteasome. Such a model will be useful for screening for compounds that increase target protein localization to the proteasome and/or degradation and, accordingly, will be useful for the development of therapeutic compounds for treating disorders associated with protein expression and/or activity (e.g., promote localization to the proteasome). It will, additionally, be useful in the formulation of protein-based and/or polypeptide-based drugs whose activity can be regulated in a temporal-specific manner (e.g., activated or deactivated when it is desirable to do so) by means of localization to the proteasome and/or degradation. It will also be useful as a research tool for the study of protein function in the context of systems biology.

EXAMPLE VII

Methods

Construction of Parental Strain DY001

Primer and plasmid sequence information is set forth below. All experiments were performed in derivatives of strain DY001 to ensure that the components of the heterodimerization system would minimally interact with endogenous proteins, thus preventing cell cycle arrest and mislocalization of the reporter upon the addition of rapamycin (Heitman et al. (1991) *Science* 253:905). The Fpr1-rapamycin binding domain (nucleotides 5656-6243) of the dominant allele TOR1-2 was amplified from strain JHY17-9C (Lorenz et al. (1995) *J. Biol. Chem.* 270:27531) and subcloned into the integrating plasmid pRS306 (Sikorski et al. (1989) *Genetics* 122:19). This vector was then digested with HindIII to cut once within TOR1-2 and transformed into the strain BY4742 Δfpr1::kan$^r$ (Research Genetics). Integration and subsequent loop-out was selected for on the appropriate plates. The correct strain was verified by PCR and sequencing.

Genomic Tagging of Proteasome Subunits

Tagging of proteasome subunits was performed both by homologous recombination of linear fragments containing 40 bp of flanking homology to the target site[i] and by two-step integration with a non-replicating plasmid[ii].

[i] FPR1 was amplified by PCR from the strain FY4 (Winston et al. (1995) *Yeast* 11:53) and subcloned into the plasmid pUG-spHIS5 (Wach et al. (1997) *Yeast* 13:1065) with a C-terminal HA-tag, forming FPR1-HA-pUG-spHIS5. Integration primers pairs were designed for tagging each of the four proteasome subunits (PRE10, RPN2, RPN6, RPN11). For each pair, one primer contained 40 bp of genomic homology to the 3' end of the proteasome subunit, excluding the stop codon, and 20 bp of homology to the 5' of FPR1 on pUG-spHIS5, excluding ATG. The second primer contained 40 bp of genomic homology approximately 50 bp downstream of the proteasome subunit gene stop codon and 20 bp of homology to pUG-spHIS5 immediately downstream of the spHIS5 marker flanked by loxP sites. Two confirmatory primers were also designed that flanked the integration site of each proteasome subunit. Strain DY001 was transformed with pSH47, a plasmid with a galactose-inducible cre gene and a URA3 selection marker (Guldener et al. (1996) *Nucleic Acids Res.* 24:2519). A 2 kb linear fragment from FPR1-HA-pUG-spHIS5 was amplified using each integration primer pair to generate linear 2 kb fragments suitable for genomic integration. 15 µg of each fragment was transformed into DY001 carrying pSH47 and selection was performed on SC-URA-HIS. Colonies were then picked and streaked onto SC-URA GAL to induce cre and to select for the loopout of the spHIS5 marker. Colonies were finally streaked onto a 5-fluoroorotic acid containing plate to remove pSH47. All tagged subunits were verified by sequencing.

[ii] Approximately 400-500 bp of the carboxy-terminal end (without the stop codon) and 3' untranslated region of proteasome subunits RPT2, RPT5, and RPN10 were amplified from strain FY4. Each pair was subcloned into the integration plasmid pRS306 (Sikorski et al. (1989) *Genetics* 122:19) along with FPR1 so that the final structure at the cloning site was 5'-proteasome subunit C-term—FPR1—proteasome subunit UTR. Each derivative of pRS306 was cut at a unique site within the carboxy-terminus of the proteasome subunit and transformed into DY001. Selection for integration was done on SC-URA, loopout of the marker was on 5-fluoroorotic acid containing plates. All tagged subunits were verified by sequencing.

Δpdr5 strains were generated by recombination of a URA3 marker flanked by 40 bp homologous to sequence immediately 5' and 3' to genomic PDR5.

Preparation of Reporter Plasmids

All versions of the reporters were derivatives of the vector pRS415 (Sikorski et al. (1989) *Genetics* 122:19). TOR1 (S1972R) is an allele of TOR1 that has a severely impaired binding affinity to FPR1-rapamycin (Heitman et al. (1991) *Science* 253:905). The sequence corresponding to amino acids 1883-2078 for both Tor1 and Tor1 (S1972R) were amplified and inserted into the vector pRS415 along with HIS3 amplified from strain FY4. HA-tagged versions of the reporters had the hemagglutinin epitope fused C-terminal to His3.

Screen and Western Assays

In both assays, rapamycin was added to a final concentration of 1 µM, cycloheximide was added to a final concentration of 30 ng/ml and PS-341 was added to a final concentration of 200 µM. For liquid cultures, samples were extracted at fixed time intervals (0, 30, 60, 90 minutes) and whole cell extracts were made. 25 µg of total protein was used from each sample, resolved by SDS-PAGE and transferred to PVDF membranes. Membranes were blocked with 10% powdered nonfat milk in PBST overnight at 4° C. and incubated with anti-HA (3F10) primary antibody (Roche Diagnostics, Indianapolis, Ind.), then HP-conjugated anti-rat secondary antibody. Visualization was done using the ECL Western Blotting system (Amersham Biosciences, Piscataway, N.J.).

Purification of the Proteasome 26S proteasomes were affinity purified from strains Pre10-FPR1 and Rpn10 FPR1 using the Rpn11-TEV-ProA tag described previously (Leggett et al. (2002) *Mol. Cell* 10:495). Cells were grown in YPD, harvested, resuspended in 50 mM Tris-HCl [pH 8], 1 mM EDTA and lysed by French press. Lysates was centrifuged at 15,000×g for 25 minutes, filtered and incubated with IgG resin (ICN) for 1 hr at 4° C. Resin was collected in a column, washed with 100 bed volumes of 50 mM Tris-HCl [pH 8], 50 mM NaCl, 1 mM EDTA buffer and equilibrated with TEV-protease buffer (50 mM Tris-HCl [pH 7.5], 1 mM EDTA, 1 mM DTT). Elution was performed by incubating the resin in 1.5 bed volumes of TEV-protease buffer containing 50 U of 6 His-TEV-protease per ml of resin, at 30° C. for 1 hour. One single homogeneous fraction was collected and aliquoted for each prep. The integrity of the 26S complexes and presence of Pre10-FPR1 and Rpn10-FPR1 tagged subunits was analyzed by Coomassie staining, SDS-PAGE and immunodetection.

In Vitro Assay

HA-tagged TOR-HIS3 and $TOR_{S1972R}$-HIS3 were cut out of their respective pRS415 vectors, inserted into PRO-Tet.133 and transformed into DH5αPRO cells (BD Biosciences). A 10 ml overnight culture was used to inoculate 1 L of media, which was subsequently growth for 4 hours at 37° C. The fusion protein production was induced with 100 ng/ml of anhydrotetracycline and the culture was growth for four hours at 30° C. Isolation of purified protein was done according to the manufacturers instructions, using a bead bed volume of 250 µl. 1.5 ml of the eluate was dialyzed against 50 mM Tris-HCl [pH 7.5], 1 mM EDTA and concentrated to approximately 1 mg/ml. The assays were performed in activity buffer (50 mM Tris-HCl [pH 7.5], 5 mM $MgCl_2$, 1 mM EDTA, 5 mM ATP) containing 4 µg of proteasome and 1.6 µg of Tor-His3 or $Tor_{S1972R}$-His3, in an initial volume of 100 µl, at 30° C. Heterodimerization was induced with 1 µM rapamycin and proteasome activity was inhibited with 100 µM PS-341. Time course fractions were obtained by extraction of equal volumes from the reaction tub in regular intervals.

Plasmids

Plasmid pUG-spHIS5-FPR1HA was used to create strain Pre10-FPR1 by double homologous recombination of a linear amplified PCR product. Plasmid pRS306-Rpn10-FPR1 was cut with KasI and used to create strain Rpn10-FPR1 by two-step integration.

```
P415-TOR-HIS3:
TCGCGCGTTTCGGTGATGACGGTGAAAACCTCTGACACATGCAGCTCCCGGA    (SEQ ID NO:1)
GACGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGCAT
CAGAGCAGATTGTACTGAGAGTGCACCATATCGACTACGTCGTAAGGCCGTT
TCTGACAGAGTAAAATTCTTGAGGGAACTTTCACCATTATGGGAAATGGTTC
AAGAAGGTATTGACTTAAACTCCATCAAATGGTCAGGTCATTGAGTGTTTTTT
ATTTGTTGTATTTTTTTTTTTTAGAGAAAATCCTCCAATATCAAATTAGGAAT
CGTAGTTTCATGATTTTCTGTTACACCTAACTTTTTGTGTGGTGCCCTCCTCCT
TGTCAATATTAATGTTAAAGTGCAATTCTTTTTCCTTATCACGTTGAGCCATTA
GTATCAATTTGCTTACCTGTATTCCTTTACTATCCTCCTTTTTCTCCTTCTTGAT
AAATGTATGTAGATTGCGTATATAGTTTCGTCTACCCTATGAACATATTCCAT
TTTGTAATTTCGTGTCGTTTCTATTATGAATTTCATTTATAAAGTTTATGTACA
AATATCATAAAAAAAGAGAATCTTTTTAAGCAAGGATTTTCTTAACTTCTTCG
GCGACAGCATCACCGACTTCGGTGGTACTGTTGGAACCACCTAAATCACCAG
TTCTGATACCTGCATCCAAAACCTTTTTAACTGCATCTTCAATGGCCTTACCTT
CTTCAGGCAAGTTCAATGACAATTTCAACATCATTGCAGCAGACAAGATAGT
GGCGATAGGGTCAACCTTATTCTTTGGCAAATCTGGAGCAGAACCGTGGCAT
GGTTCGTACAAACCAAATGCGGTGTTCTTGTCTGGCAAAGAGGCCAAGGACG
CAGATGGCAACAAACCCAAGGAACCTGGGATAACGGAGGCTTCATCGGAGA
TGATATCACCCAAACATGTTGCTGGTGATTATAATACCATTTAGGTGGGTTGGG
TTCTTAACTAGGATCATGGCGGCAGAATCAATCAATTGATGTTGAACCTTCAA
TGTAGGGAATTCGTTCTTGATGGTTTCCTCCACAGTTTTTCTCCATAATCTTGA
AGAGGCCAAACATTAGCTTTATCCAAGGACCAAATAGGCAATGGTGGCTCA
TGTTGTAGGGCCATGAAAGCGGCCATTCTTGTGATTCTTTGCACTTCTGGAAC
GGTGTATTGTTCACTATCCCAAGCGACACCATCACCATCGTCTTCCTTTCTCTT
ACCAAAGTAAATACCTCCCACTAATTCTCTGACAACAACGAAGTCAGTACCT
TTAGCAAATTGTGGCTTGATTGGAGATAAGTCTAAAAGAGAGTCGGATGCAA
AGTTACATGGTCTTAAGTTGGCGTACAATTGAAGTTCTTTACGGATTTTTAGT
AAACCTTGTTCAGGTCTAACACTACCGGTACCCCATTTAGGACCACCCACAG
CACCTAACAAAACGGCATCAACCTTCTTGGAGGCTTCCAGCGCCTCATCTGG
AAGTGGGACACCTGTAGCATCGATAGCAGCACCACCAATTAAATGATTTTCG
AAATCGAACTTGACATTGGAACGAACATCAGAAATAGCTTTAAGAACCTTAA
TGGCTTCGGCTGTGATTTCTTGACCAACGTGGTCACCTGGCAAAACGACGATC
TTCTTAGGGGCAGACATAGGGGCAGACATTAGAATGGTATATCCTTGAAATA
TATATATATATTGCTGAAATGTAAAAGGTAAGAAAAGTTAGAAAGTAAGACG
ATTGCTAACCACCTATTGGAAAAAACAATAGGTCCTTAAATAATATTGTCAA
CTTCAAGTATTGTGATGCAAGCATTTAGTCATGAACGCTTCTCTATTCTATAT
GAAAAGCCGGTTCCGGCCTCTCACCTTTCCTTTTTCTCCCAATTTTTCAGTTGA
AAAAGGTATATGCGTCAGGCGACCTCTGAAATTAACAAAAAATTTCCAGTCA
TCGAATTTGATTCTGTGCGATAGCGCCCCTGTGTGTTCTCGTTATGTTGAGGA
```

-continued

```
AAAAAATAATGGTTGCTAAGAGATTCGAACTCTTGCATCTTACGATACCTGA
GTATTCCCACAGTTAACTGCGGTCAAGATATTTCTTGAATCAGGCGCCTTAGA
CCGCTCGGCCAAACAACCAATTACTTGTTGAGAAATAGAGTATAATTATCCT
ATAAATATAACGTTTTTGAACACACATGAACAAGGAAGTACAGGACAATTGA
TTTTGAAGAGAATGTGGATTTTGATGTAATTGTTGGGATTCCATTTTTAATAA
GGCAATAATATTAGGTATGTGGATATACTAGAAGTTCTCCTCGACCGTCGATA
TGCGGTGTGAAATACCGCACAGATGCGTAAGGAGAAAATACCGCATCAGGA
AATTGTAAACGTTAATATTTTGTTAAAATTCGCGTTAAATTTTTGTTAAATCA
GCTCATTTTTTAACCAATAGGCCGAAATCGGCAAAATCCCTTATAAATCAAA
AGAATAGACCGAGATAGGGTTGAGTGTTGTTCCAGTTTGGAACAAGAGTCCA
CTATTAAAGAACGTGGACTCCAACGTCAAAGGGCGAAAAACCGTCTATCAGG
GCGATGGCCCACTACGTGAACCATCACCCTAATCAAGTTTTTTGGGGTCGAG
GTGCCGTAAAGCACTAAATCGGAACCCTAAAGGGAGCCCCCGATTTAGAGCT
TGACGGGGAAAGCCGGCGAACGTGGCGAGAAAGGAAGGGAAGAAAGCGAA
AGGAGCGGGCGCTAGGGCGCTGGCAAGTGTAGCGGTCACGCTGCGCGTAAC
CACCACACCCGCCGCGCTTAATGCGCCGCTACAGGGCGCGTCGCGCCATTCG
CCATTCAGGCTGCGCAACTGTTGGGAAGGGCGATCGGTGCGGGCCTCTTCGC
TATTACGCCAGCTGGCGAAAGGGGGATGTGCTGCAAGGCGATTAAGTTGGGT
AACGCCAGGGTTTTCCCAGTCACGACGTTGTAAAACGACGGCCAGTGAGCGC
GCGTAATACGACTCACTATAGGGCGAATTGGGTACCGGTACCGGCCGCAAAT
TAAAGCCTTCGAGCGTCCCAAAACCTTCTCAAGCAAGGTTTTCAGTATAATGT
TACATGCGTACACGCGTCTGTACAGAAAAAAAAGAAAAATTTGAAATATAAA
TAACGTTCTTAATACTAACATAACTATAAAAAAATAAATAGGGACCTAGACT
TCAGGTTGTCTAACTCCTTCCTTTTCGGTTAGAGCGGATGTGGGGGGAGGGCG
TGAATGTAAGCGTGACATAACTAATTACATGACCTCGAGGTCGACGGTATCG
ATAAGCTTGATATCGAATTCCTGCAGCCCGGGGGATCCCTACATAAGAACAC
CTTTGGTGGAGGGAACATCGTTGGTACCATTGGGCGAGGTGGCTTCTCTTATG
GCAACCGCAAGAGCCTTGAACGCACTCTCACTACGGTGATGATCATTCTTGC
CTCGCAGACAATCAACGTGGAGGGTAATTCTGCTAGCCTCTGCAAAGCTTTC
AAGAAAATGCGGGATCATCTCGCAAGAGAGATCTCCTACTTTCTCCCTTTGCA
AACCAAGTTCGACAACTGCGTACGGCCTGTTCGAAAGATCTACCACCGCTCT
GGAAAGTGCCTCATCCAAAGGCGCAAATCCTGATCCAAACCTTTTTACTCCA
CGCACGGCCCCTAGGGCCTCTTTAAAAGCTTGACCGAGAGCAATCCCGCAGT
CTTCAGTGGTGTGATGGTCGTCTATGTGTAAGTCACCAATGCACTCAACGATT
AGCGACCAGCCGGAATGCTTGGCCAGAGCATGTATCATATGGTCCAGAAACC
CTATACCTGTGTGGACGTTAATCACTTGCGATTGTGTGGCCTGTTCTGCTACT
GCTTCTGCCTCTTTTTCTGGGAAGATCGAGTGCTCTATCGCTAGGGGACCACC
CTTTAAAGAGATCGCAATCTGAATCTTGGTTTCATTTGTAATACGCTTTACTA
GGGCTTTCTGCTCTGTGGCTCGAGCAGGAACAGCCAATTCGAGATCATGAGT
AGCCAGAAGCTGGGGAGAAACATGCTGTAAGTCTAAGGTTTGTAACTGTGGT
ATTTGACGTGTTATTTTTCTGAAGACGTTATAATAAATATCCCAAGCTTGGTT
CAAATTATTGATGTCTTTTGACTTTTTGTAGTTATTCAACCATTCGTAGGCATC
GTTCAAATCTCTACCAAATGATTTCTGAAACGATACCTCACTTAACGTTTGAG
GCTCATTGCCTAAGTGTTTATGTAAAGGTTCTAAAGTAGAAAACATTTTTTCT
ATGTTATTCAACGAAAAATTGGCGGCTCGCATCTTCCAGTCCTTCATACCA
TAATTCGTGCCATAGAACGGCTACTCTGATCAACTCGTGACTAACTAATTCTG
CCTGGTTTACCAGGACTGGACTATGAATCCTAATTTTCTCTATTATTGAAAGA
GCCGCTTTTTGTCTTGAAACAGATTCAGACTTGATCGCGACAGTTAAAGGATA
CACGAGAGCTTGTGGATGAGCTTTCCCTAAATCAGAAAGCAACGACAAAAGG
GAATTACTCACCGTAGGATCTGGCTGATGTATCATGGATCCACTAGTTCTAGA
GCGGCCAGCTTGGAGTTGATTGTATGCTTGGTATAGCTTGAAATATTGTGCAG
AAAAAGAAACAAGGAAGAAAGGGAACGAGAACAATGACGAGGAAACAAA
GATTAATAATTGCAGGTCTATTTATACTTGATAGCAAAGCGGCAAACTTTTTT
TATTTCAAATTCAAGTAACTGGAAGGAAGGCCGTATACCGTTGCTCATTAGA
GAGTAGTGTGCGTGAATGAAGGAAGGAAAAAGTTTCGTGTGTTCGAAGATAC
CCCTCATCAGCTCTGGAACAACGACATCTGTTGGTGCTGTCTTTGTCGTTAAT
TTTTTCCTTTAGTGTCTTCCATCATTTTTTTTGTCATTGCGGATATGGTGAGAC
AACAACGGGGAGAGAAAAGAAAAAAAAAGAAAAGAAGTTGCATGCGC
CTATTATTACTTCAATAGATGGCAAATGGAAAAAGGGTAGTGAAACTTCGAT
ATGATGATGGCTATCAAGTCTAGGGCTACAGTATTAGTTCGTTATGTACCACC
ATCAATGAGGCAGTGTAATTGGTGTAGTCTTGTTTAGCCCATTATGTCTTGTC
TGGTATCTGTTCTATTGTATATCTCCCCTCCGCCACCTACATGTTAGGGAGAC
CAACGAAGGTATTATAGGAATCCCGATGTATGGGTTTGGTTGCCAGAAAAGA
GGAAGTCCATATTGTACACCCGGAAACAACAAAAGGATATCCGAAATATTCC
ACGGTTTAGAAAAAAATCGGAAAAGAGCGCGGAGGGGTGTTACCCCCCTTCT
CTACTAGCATTGGACTTTAATTAATATATGTGCATAGGAGAAGTGTAAAGTTC
CCTTCCATATTGTAACATAATAAAGTGCACACCCAAATGAATTGAAAGCGTA
CTCAAACAGACAACCATTTCCAGTGTTGTATGTACCTGTCTATTTATACTGGT
AGCAACCCTATTGCTGTTTCCTCTTCAAAGTACTCTAGCGGTTATGCGCGTCT
CACCTTCAAGGTCATGGTCGCTCTATTGTTCGCACCACCGGCAAACTCGCGTC
TCGCAAGTCTTGGCTCATTCTTCTAGTATACTCATGTTGCAAATGCACTCAGG
TTCTTTCGGCAACTTAAATAATGACACCAGTTGTCGTGGTCGTCATCATCGCA
ACCCCAACCGGCATTCTTATTGCTTCTCCAATCTCGCCCCTTAGCGCAGGGTA
AACCTTGGAAAATGCAGGCGCAAAAAACTCCGCCGGGCACAGCCTCACGCCC
AGCGTTATCGCCGGGCCGGCAAGAGCGCGGGTCCGCCACAGAGTCAGCATG
ATTGTGCAATTGCGTAAACTCGTTTTTTCGGCGCCGCAAAGCCAAATACATCA
TATCAACACTTTTCACTTTATTTTTCGTTCGACCCTTATATTTGTCTTTTGCCTT
CATGCTCCTTGATTTCCTATTTCATTTACCATCATTTCTTGAGCTCCAGCTTTT
GTTCCCTTTAGTGAGGGTTAATTGCGCGCTTGGCGTAATCATGGTCATAGCTG
TTTCCTGTGTGAAATTGTTATCCGCTCACAATTCCACACAACATAGGAGCCGG
```

-continued

```
AAGCATAAAGTGTAAAGCCTGGGGTGCCTAATGAGTGAGGTAACTCACATTA
ATTGCGTTGCGCTCACTGCCCGCTTTCCAGTCGGGAAACCTGTCGTGCCAGCT
GCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCG
AGCGGTATCAGCTCACTCAAAGGCGGTAATACGGTTATCCACAGAATCAGGG
GATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCGTTCG
CTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGTTTG
CAAGCAGCAGATTACGCGCAGAAAAAAAGGATCTCAAGAAGATCCTTTGATC
TTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAT
GAAGTTTTAAATCAATCTAAAGTATATATGAGTAAACTTGGTCTGACAGTTAC
CAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTA
CCATCTGGCCCCAGTGCTGCAATGATACCGCGAGACCCACGCTCACCGGCTC
CAGATTTATCAGCAATAAACCAGCCAGCCGGAAGGGCCGAGCGCAGAAGTG
GTCCTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGCTAC
AGGCATCGTGGTGTCACGCTCGTCGTTTGGTATGGCTTCATTCAGCTCCGGTT
CCCAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTG
TATGCGGCGACCGAGTTGCTCTTGCCCGGCGTCAATACGGGATAATACCGCG
CCACATAGCAGAACTTTAAAAGTGCTCATCATTGGAAAACGTTCTTCGGGGC
GAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTG
AGCAAAAACAGGAAGGCAAAATGCCGCAAAAAAGGGAATAAGGGCGACAC
GGAAATGTTGAATACTCATACTCTTCCTTTTTCAATATTATTGAAGCATTTATC
AGGGTTATTGTCTCATGAGCGGATACATATTTGAATGTATTTAGAAAAATAA
ACAAATAGGGGTTCCGCGCACATTTCCCCGAAAAGTGCCACCTGGGTCCTTTT
CATCACGTGCTATAAAAATAATTATAATTTAAATTTTTTAATATAAATATATA
AATTAAAAATAGAAAGTAAAAAAAGAAATTAAAGAAAAAATAGTTTTTGTTT
TCCGAAGATGTAAAAGACTCTAGGGGATCGCCAACAAATACTACCTTTTAT
CTTGCTCTTCCTGCTCTCAGGTATTAATGCCGAATTGTTTCATCTTGTCTGTGT
AGAAGACCACACACGAAAATCCTGTGATTTTACATTTTACTTATCGTTAATCG
AATGTATATCTATTTAATCTGCTTTTCTTGTCTAATAAATATATATGTAAAGTA
CGCTTTTTGTTGAAATTTTTTAAACCTTTGTTTATTTTTTTTCTTCATTCCGTA
ACTCTTCTACCTTCTTTATTTACTTTCTAAAATCCAAATACAAAACATAAAAA
TAAATAAACACAGAGTAAATTCCCAAATTATTCCATCATTAAAAGATACGAG
GCGCGTGTAAGTTACAGGCAAGCGATCCGTCCTAAGAAACCATTATTATCAT
GACATTAACCTATAAAAATAGGCGTATCACGAGGCCCTTTCGTC
P415-TOR-link-HIS3HA:
TCGCGCGTTTCGGTGATGACGGTGAAAACCTCTGACACATGCAGCTCCCGGA    (SEQ ID NO:2)
GACGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGCAT
CAGAGCAGATTGTACTGAGAGTGCACCATATCGACTACGTCGTAAGGCCGTT
TCTGACAGAGTAAAATTCTTGAGGGAACTTTCACCATTATGGGAAATGGTTC
AAGAAGGTATTGACTTAAACTCCATCAAATGGTCAGGTCATTGAGTGTTTTTT
ATTTGTTGTATTTTTTTTTTTTTAGAGAAAATCCTCCAATATCAAATTAGGAAT
CGTAGTTTCATGATTTTCTGTTACACCTAACTTTTTGTGTGGTGCCCTCCTCCT
TGTCAATATTAATGTTAAAGTGCAATTCTTTTTCCTTATCACGTTGAGCCATTA
GTATCAATTTGCTTACCTGTATTCCTTTACTATCCTCCTTTTTCTCCTTCTTGAT
AAATGTATGTAGATTGCGTATATAGTTTCGTCTACCCTATGAACATATTCCAT
TTTGTAATTTCGTGTCGTTTCTATTATGAATTTCATTTATAAAGTTTATGTACA
AATATCATAAAAAAAGAGAATCTTTTTAAGCAAGGATTTTCTTAACTTCTTCG
GCGACAGCATCACCGACTTCGGTGGTACTGTTGGAACCACCTAAATCACCAG
TTCTGATACCTGCATCCAAAACCTTTTTAACTGCATCTTCAATGGCCTTACCTT
CTTCAGGCAAGTTCAATGACAATTTCAACATCATTGCAGCAGACAAGATAGT
GGCGATAGGGTCAACCTTATTCTTTGGCAAATCTGGAGCAGAACCGTGGCAT
GGTTCGTACAAACCAAATGCGGTGTTCTTGTCTGGCAAAGAGGCCAAGGACG
CAGATGGCAACAAACCCAAGGAACCTGGGATAACGGAGGCTTCATCGGAGA
TGATATCACCAAACATGTTGCTGGTGATTATAATACCATTTAGGTGGGTTGGG
TTCTTAACTAGGATCATGGCGGCAGAATCAATCAATTGATGTTGAACCTTCAA
TGTAGGGAATTCGTTCTTGATGGTTTCCTCCACAGTTTTTCTCCATAATCTTGA
AGAGGCCAAAACATTAGCTTTATCCAAGGACCAAATAGGCAATGGTGGCTCA
TGTTGTAGGGCCATGAAAGCGGCCATTCTTGTGATTCTTTGCACTTCTGGAAC
GGTGTATTGTTCACTATCCCAAGCGACACCATCACCATCGTCTTCCTTTCTCTT
ACCAAAGTAAATACCTCCCACTAATTCTCTGACAACAACGAAGTCAGTACCT
TTAGCAAATTGTGGCTTGATTGGAGATAAGTCTAAAAGAGAGTCGGATGCAA
AGTTACATGGTCTTAAGTTGGCGTACAATTGAAGTTCTTTACGGATTTTTAGT
```

```
                        -continued
AAACCTTGTTCAGGTCTAACACTACCGGTACCCCATTTAGGACCACCCACAG
CACCTAACAAAACGGCATCAACCTTCTTGGAGGCTTCCAGCGCCTCATCTGG
AAGTGGGACACCTGTAGCATCGATAGCAGCACCACCAATTAAATGATTTTCG
AAATCGAACTTGACATTGGAACGAACATCAGAAATAGCTTTAAGAACCTTAA
TGGCTTCGGCTGTGATTTCTTGACCAACGTGGTCACCTGGCAAAACGACGATC
TTCTTAGGGGCAGACATAGGGGCAGACATTAGAATGGTATATCCTTGAAATA
TATATATATATTGCTGAAATGTAAAAGGTAAGAAAAGTTAGAAAGTAAGACG
ATTGCTAACCACCTATTGGAAAAAACAATAGGTCCTTAAATAATATTGTCAA
CTTCAAGTATTGTGATGCAAGCATTTAGTCATGAACGCTTCTCTATTCTATAT
GAAAAGCCGGTTCCGGCCTCTCACCTTTCCTTTTTCTCCCAATTTTTCAGTTGA
AAAAGGTATATGCGTCAGGCGACCTCTGAAATTAACAAAAAATTTCCAGTCA
TCGAATTTGATTCTGTGCGATAGCGCCCCTGTGTGTTCTCGTTATGTTGAGGA
AAAAAATAATGGTTGCTAAGAGATTCGAACTCTTGCATCTTACGATACCTGA
GTATTCCCACAGTTAACTGCGGTCAAGATATTTCTTGAATCAGGCGCCTTAGA
CCGCTCGGCCAAACAACCAATTACTTGTTGAGAAATAGAGTATAATTATCCT
ATAAATATAACGTTTTTGAACACACATGAACAAGGAAGTACAGGACAATTGA
TTTTGAAGAGAATGTGGATTTTGATGTAATTGTTGGGATTCCATTTTTAATAA
GGCAATAATATTAGGTATGTGGATATACTAGAAGTTCTCCTCGACCGTCGATA
TGCGGTGTGAAATACCGCACAGATGCGTAAGGAGAAAATACCGCATCAGGA
AATTGTAAACGTTAATATTTTGTTAAAATTCGCGTTAAATTTTTGTTAAATCA
GCTCATTTTTTAACCAATAGGCCGAAATCGGCAAAATCCCTTATAAATCAAA
AGAATAGACCGAGATAGGGTTGAGTGTTGTTCCAGTTTGGAACAAGAGTCCA
CTATTAAAGAACGTGGACTCCAACGTCAAAGGGCGAAAAACCGTCTATCAGG
GCGATGGCCCACTACGTGAACCATCACCCTAATCAAGTTTTTTGGGGTCGAG
GTGCCGTAAAGCACTAAATCGGAACCCTAAAGGGAGCCCCCGATTTAGAGCT
TGACGGGGAAAGCCGGCAACGTGGCGAGAAAGGAAGGGAAGAAAGCGAA
AGGAGCGGGCGCTAGGGCGCTGGCAAGTGTAGCGGTCACGCTGCGCGTAAC
CACCACACCCGCCGCGCTTAATGCGCCGCTACAGGGCGCGTCGCGCCATTCG
CCATTCAGGCTGCGCAACTGTTGGGAAGGGCGATCGGTGCGGGCCTCTTCGC
TATTACGCCAGCTGGCGAAAGGGGGATGTGCTGCAAGGCGATTAAGTTGGGT
AACGCCAGGGTTTTCCCAGTCACGACGTTGTAAAACGACGGCCAGTGAGCGC
GCGTAATACGACTCACTATAGGGCGAATTGGGTACCGGTACCGGCCGCAAAT
TAAAGCCTTCGAGCGTCCCAAAACCTTCTCAAGCAAGGTTTTCAGTATAATGT
TACATGCGTACACGCGTCTGTACAGAAAAAAAAGAAAAATTTGAAATATAAA
TAACGTTCTTAATACTAACATAACTATAAAAAAATAAATAGGGACCTAGACT
TCAGGTTGTCTAACTCCTTCCTTTTCGGTTAGAGCGGATGTGGGGGGAGGGCG
TGAATGTAAGCGTGACATAACTAATTACATGACCTCGAGGTCGACTTAAGCG
TAATCTGGAACATCGTATGGGTACTGCAGCATAAGAACACCTTTGGTGGAGG
GAACATCGTTGGTACCATTGGGCGAGGTGGCTTCTCTTATGGCAACCGCAAG
AGCCTTGAACGCACTCTCACTACGGTGATGATCATTCTTGCCTCGCAGACAAT
CAACGTGGAGGGTAATTCTGCTAGCCTCTGCAAAGCTTTCAAGAAAATGCGG
GATCATCTCGCAAGAGAGATCTCCTACTTTCTCCCTTTGCAAACCAAGTTCGA
CAACTGCGTACGGCCTGTTCGAAAGATCTACCACCGCTCTGGAAAGTGCCTC
ATCCAAAGGCGCAAATCCTGATCCAAACCTTTTTACTCCACGCACGGCCCCTA
GGGCCTCTTTAAAAGCTTGACCGAGAGCAATCCCGCAGTCTTCAGTGGTGTG
ATGGTCGTCTATGTGTAAGTCACCAATGCACTCAACGATTAGCGACCAGCCG
GAATGCTTGGCCAGAGCATGTATCATATGGTCCAGAAACCCTATACCTGTGT
GGACGTTAATCACTTGCGATTGTGTGGCCTGTTCTGCTACTGCTTCTGCCTCTT
TTTCTGGGAAGATCGAGTGCTCTATCGCTAGGGGACCACCCTTTAAAGAGAT
CGCAATCTGAATCTTGGTTTCATTTGTAATACGCTTTACTAGGGCTTTCTGCTC
TGTGCGGCCGCTGCCGCCCGTACGGGAACTATGCATCTCTGAGGAATGGTCTT
CTCCTCCAACAAAACACCTAGGAGGAACAGCCAATTCGAGATCATGAGTAGC
CAGAAGCTGGGGAGAAACATGCTGTAAGTCTAAGGTTTGTAACTGTGGTATT
TGACGTGTTATTTTTCTGAAGACGTTATAATAAATATCCCAAGCTTGGTTCAA
ATTATTGATGTCTTTTGACTTTTTGTAGTTATTCAACCATTCGTAGGCATCGTT
CAAATCTCTACCAAATGATTTCTGAAACGATACCTCACTTAACGTTTGAGGCT
CATTGCCTAAGTGTTTATGTAAAGGTTCTAAAGTAGAAAACATTTTTTCTATG
TTATGTTCAACGAAAAATTGGCGGCTCGCATCTTCCAGTCCTTCATACCATAA
TTCGTGCCATAGAACGGCTACTCTGATCAACTCGTGACTAACTAATTCTGCCT
GGTTTACCAGGACTGGACTATGAATCCTAATTTTCTCTATTATTGAAAGAGCC
GCTTTTTGTCTTGAAACAGATTCAGACTTGATCGCGACAGTTAAAGGATACAC
GAGAGCTTGTGGATGAGCTTTCCCTAAATCAGAAAGCAACGACAAAAGGGA
ATTACTCACCGTAGGATCTGGCTGATGTATCATGGATCCACTAGTTCTAGAGC
GGCCAGCTTGGAGTTGATTGTATGCTTGGTATAGCTTGAAATATTGTGCAGAA
AAAGAAACAAGGAAGAAAGGGAACGAGAACAATGACGAGGAAACAAAGA
TTAATAATTGCAGGTCTATTTATACTTGATAGCAAAGCGGCAAACTTTTTTTA
TTTCAAATTCAAGTAACTGGAAGGAAGGCCGTATACCGTTGCTCATTAGAGA
GTAGTGTGCGTGAATGAAGGAAGGAAAAAGTTTCGTGTGTTCGAAGATACCC
CTCATCAGCTCTGGAACAACGACATCGTTGGTGCTGTCTTTGTCGTTAATTTT
TTCCTTTAGTGTCTTCCATCATTTTTTTTGTCATTGCGGATATGGTGAGACAAC
AACGGGGAGAGAAAAGAAAAAAAAAAGAAAAGAAGTTGCATGCGCCTAT
TATTACTTCAATAGATGGCAAATGGAAAAAGGGTAGTGAAACTTCGATATGA
TGATGGCTATCAAGTCTAGGGCTACAGTATTAGTTCGTTATGTACCACCATCA
ATGAGGCAGTGTAATTGGTGTAGTCTTGTTTAGCCCATTATGTCTTGTCTGGT
ATCTGTTCTATTGTATATCTCCCCTCCGCCACCTACATGTTAGGGAGACCAAC
GAAGGTATTATAGGAATCCCGATGTATGGGTTTGGTTGCCAGAAAAGAGGAA
GTCCATATTGTACACCCGGAAACAACAAAAGGATATCCGAAATATTCCACGG
TTTAGAAAAAAATCGGAAAAGAGCGCGGAGGGGTGTTACCCCCCTTCTCTAC
TAGCATTGGACTTTAATTAATATATGTGCATAGGAGAAGTGTAAAGTTCCCTT
CCATATTGTAACATAATAAAGTGCACACCCAAATGAATTGAAAGCGTACTCA
```

-continued

```
AACAGACAACCATTTCCAGTGTTGTATGTACCTGTCTATTTATACTGGTAGCA
ACCCTATTGCTGTTTCCTCTTCAAAGTACTCTAGCGGTTATGCGCGTCTCACCT
TCAAGGTCATGGTCGCTCTATTGTTCGCACCACCGGCAAACTCGCGTCTCGCA
AGTCTTGGCTCATTCTTCTAGTATACTCATGTTGCAAATGCACTCAGGTTCTTT
CGGCAACTTAAATAATGACACCAGTTGTCGTGGTCGTCATCATCGCAACCCC
AACCGGCATTCTTATTGCTTCTCCAATCTCGCCCCTTAGCGCAGGGTAAACCT
TGGAAAATGCAGGCGCAAAAAACTCCGCCGGGCACAGCCTCACGCCCAGCG
TTATCGCCGGGCCGGCAAGAGCGCGGGTCCGCCACAGAGTCAGCATGATTGT
GCAATTGCGTAAACTCGTTTTTTCGGCGCCGCAAAGCCAAATACATCATATCA
ACACTTTTCACTTTATTTTTCGTTCGAC-
CCTTATATTTTGTCTTTTGCCTTCATGC
TCCTTGATTTCCTATTTCATTTACCATCATTTCTTGAGCTCCAGCTTTTGTTCCC
TTTAGTGAGGGTTAATTGCGCGCTTGGCGTAATCATGGTCATAGCTGTTTCCT
GTGTGAAATTGTTATCCGCTCACAATTCCACACAACATAGGAGCCGGAAGCA
TAAAGTGTAAAGCCTGGGGTGCCTAATGAGTGAGGTAACTCACATTAATTGC
GTTGCGCTCACTGCCCGCTTTCCAGTCGGGAAACCTGTCGTGCCAGCTGCATT
AATGAATCGGCCAACGCGCGGGGAGAGGCGGTTTGCGTATTGGGCGCTCTTC
CGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGCATC
ACAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGCTCCA
AGCTGGGCTGTGTGCACGAACCCCCCGTTCAGCCCGACCGCTGCGCCTTATCC
GGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTAC
AGAGTTCTTGAAGTGGTGGCCTAACTACGGCTACACTAGAAGGACAGTATTT
GGTATCTGCGCTCTGCTGAAGCCAGTTACCTTCGGAAAAAGAGTTGGTAGCT
CTTGATCCGGCAAACAAACCACCGCTGGTAGCGGTGGTTTTTTTGTTTGCAAG
CAGCAGATTACGCGCAGAAAAAAAGGATCTCAAGAAGATCCTTTGATCTTTT
CTACGGGGTCTGACGCTCAGTGGAACGAAAACTCACGTTAAGGGATTTTGGT
CATGAGATTATCAAAAAGGATCTTCACCTAGATCCTTTTAAATTAAAAATGA
AGTTTTAAATCAATCTAAAGTATATATGAGTAAACTTGGTCTGACAGTTACCA
ATGCTTAATCAGTGAGGCACCTATCTCAGCGATCTGTCTATTTCGTTCATCCA
TAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCA
GATTTATCAGCAATAAACCAGCCAGCCGGAAGGGCCGAGCGCAGAAGTGGT
CCTGCAACTTTATCCGCCTCCATCCAGTCTATTAATTGTTGCCGGGAAGCTAG
AGTAAGTAGTTCGCCAGTTAATAGTTTGCGCAACGTTGTTGCCATTGCTACAG
GCATCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTATCA
CTCATGGTTATGGCAGCACTGCATAATTCTCTTACTGTCATGCCATCCGTAAG
ATGCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGCC
ACATAGCAGAACTTTAAAAGTGCTCATCATTGGAAAACGTTCTTCGGGGCGA
AAACTCTCAAGGATCTTACCGCTGTTGAGATCCAGTTCGATGTAACCCACTCG
TGCACCCAACTGATCTTCAGCATCTTTTACTTTCACCAGCGTTTCTGGGTGAG
CAAAAACAGGAAGGCAAAATGCCGCAAAAAAGGGAATAAGGGCGACACGG
AAATGTTGAATACTCATACTCTTCCTTTTTCAATATTATTGAAGCATTTATCAG
GGTTATTGTCTCATGAGCGGATACATATTTGAATGTATTTAGAAAAATAAACA
AATAGGGGTTCCGCGCACATTTCCCCGAAAAGTGCCACCTGGGTCCTTTTCAT
CACGTGCTATAAAAATAATTATAATTTAAATTTTTTAATATAAATATATAAAT
TAAAAATAGAAAGTAAAAAAGAAATTAAAGAAAAAATAGTTTTTGTTTTCC
GAAGATGTAAAAGACTCTAGGGGATCGCCAACAAATACTACCTTTTATCTT
GCTCTTCCTGCTCTCAGGTATTAATGCCGAATTGTTTCATCTTGTCTGTGTAGA
AGACCACACACGAAATCCTGTGATTTTACATTTTACTTATCGTTAATCGAAT
GTATATCTATTTAATCTGCTTTTCTTGTCTAATAAATATATATGTAAAGTACGC
TTTTTGTTGAAATTTTTTAAACCTTTGTTTATTTTTTTTCTTCATTCCGTAACT
CTTCTACCTTCTTTATTTACTTTCTAAAATCCAAATACAAAACATAAAAATAA
ATAAACACAGAGTAAATTCCCAAATTATTCCATCATTAAAAGATACGAGGCG
CGTGTAAGTTACAGGCAAGCGATCCGTCCTAAGAAACCATTATTATCATGAC
ATTAACCTATAAAAATAGGCGTATCACGAGGCCCTTTCGTC
pUG-spHIS5-FPR1HA:
GAACGCGGCCGCCAGCTGAAGCTTCGTACGTCTGAAGTAATTGAAGGTAACG    (SEQ ID NO:3)
TCAAAATTGACAGAATTTCCCCAGGTGATGGTGCCACCTTCCCAAAGACAGG
TGACTTGGTTACCATTCATTACACCGGTACCTTGGAGAACGGCCAAAAATTCG
ATTCCTCCGTTGACAGGGGCTCTCCATTCCAATGTAACATCGGTGTCGGCCAA
GTCATCAAGGGTTGGGATGTTGGTATTCCAAAGTTGTCTGTTGGTGAAAAAG
CTAGGTTAACCATCCCTGGCCCATATGCTTATGGCCCACGTGGTTTCCCAGGT
TTGATTCCACCAAACAGTACTTTGGTTTTCGACGTCGAATTGTTGAAGGTCAA
CGGATCCTACCCATACGATGTTCCAGATTACGCTTAAGTCGACAACCCTTAAT
ATAACTTCGTATAATGTATGCTATACGAAGTTATTAGGTCTAGAGATCTGTTT
AGCTTGCCTCGTCCCCGCCGGGTCACCCGGCCAGCGACATGGAGGCCCAGAA
TACCCTCCTTGACAGTCTTGACGTGCGCAGCTCAGGGGCATGATGTGACTGTC
GCCCGTACATTTAGCCCATACATCCCCATGTATAATCATTTGCATCCATACAT
TTTGATGGCCGCACGGCGCGAAGCAAAAATTACGGCTCCTCGCTGCAGACCT
GCGAGCAGGGAAACGCTCCCCTCACAGACGCGTTGAATTGTCCCCACGCCGC
```

-continued
```
GCCCCTGTAGAGAAATATAAAAGGTTAGGATTTGCCACTGAGGTTCTTCTTTC
ATATACTTCCTTTTAAAATCTTGCTAGGATACAGTTCTCACATCACATCCGAA
CATAAACAACCATGGGTAGGAGGGCTTTTGTAGAAAGAAATACGAACGAAA
CGAAAATCAGCGTTGCCATCGCTTTGGACAAAGCTCCCTTACCTGAAGAGTC
GAATTTTATTGATGAACTTATAACTTCCAAGCATGCAAACCAAAAGGGAGAA
CAAGTAATCCAAGTAGACACGGGAATTGGATTCTTGGATCACATGTATCATG
CACTGGCTAAACATGCAGGCTGGAGCTTACGACTTTACTCAAGAGGTGATTT
AATCATCGATGATCATCACACTGCAGAAGATACTGCTATTGCACTTGGTATTG
CATTCAAGCAGGCTATGGGTAACTTTGCCGGCGTTAAAAGATTTGGACATGC
TTATTGTCCACTTGACGAAGCTCTTTCTAGAAGCGTAGTTGACTTGTCGGGAC
GGCCCTATGCTGTTATCGATTTGGGATTAAAGCGTGAAAGGTTGGGGAATT
GTCCTGTGAAATGATCCCTCACTTACTATATTCCTTTTCGGTAGCAGCTGGAA
TTACTTTGCATGTTACCTGCTTATATGGTAGTAATGACCATCATCGTGCTGAA
AGCGCTTTTAAATCTCTGGCTGTTGCCATGCGCGCGGCTACTAGTCTTACTGG
AAGTTCTGAAGTCCCAAGCACGAAGGGAGTGTTGTAAAGAGTACTGACAATA
AAAAGATTCTTGTTTTCAAGAACTTGTCATTTGTATAGTTTTTTTATATTGTAG
TTGTTCTATTTTAATCAAATGTTAGCGTGATTTATATTTTTTTCGCCTCGACA
TCATCTGCCCAGATGCGAAGTTAAGTGCGCAGAAAGTAATATCATGCGTCAA
TCGTATGTGAATGCTGGTCGCTATACTGCTGTCGATTCGATACTAACGCCGCC
ATCCAGTTTAAACGAGCTCTCGAGAACCCTTAATATAACTTCGTATAATGTAT
GCTATACGAAGTTATTAGGTGATATCAGATCCACTAGTGGCCTATGCGGCCG
CGGATCTGCCGGTCTCCCTATAGTGAGTCGTATTAATTTCGATAAGCCAGGTT
AACCTGCATTAATGAATCGGCCAACGCGCGGGGAGAGGCGGTTTGCGTATTG
GGCGCTCTTCCGCTTCCTCGCTCACTGACTCGCTGCGCTCGGTCGTTCGGCTG
CGGCGAGCGGTATCAGCTCACTCAAAGGCGGTAATACGGTTATCCACAGAAT
CAGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCCCT
GACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAA
GCGTGGCGCTTTCTCAATGCTCACGCTGTAGGTATCTCAGTTCGGTGTAGGTC
GTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTA
TCGCCACTGGCAGCAGCCACTGGTAACAGGATTAGCAGAGCGAGGTATGTAG
GCGGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAGA
GTTGGTAGCTCTTGATCCGGCAAACAAACCACCGCTGGTAGCGGTGGTTTTTT
TGTTTGCAAGCAGCAGATTACGCGCAGAAAAAAAGGATCTCAAGAAGATCCT
TTGATCTTTTCTACGGGGTCTGACGCTCAGTGGAACGAAAACTCACGTTAAGG
GATTTTGGTCATGAGATTATCAAAAAGGATCTTCACCTAGATCCTTTTAAATT
AAAAATGAAGTTTTAAATCAATCTAAAGTATATATGAGTAAACTTGGTCTGA
CAGTTACCAATGCTTAATCAGTGAGGCACCTATCTCAGCGATCTGTCTATTTC
GTTCATCCATAGTTGCCTGACTCCCCGTCGTGTAGATAACTACGATACGGGAG
GGCTTACCATCTGGCCCCAGTGCTGCAATGATACCGCGAGACCCACGCTCAC
CGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGG
GAAGCTAGAGTAAGTAGTTCGCCAGTTAATAGTTTGCGCAACGTTGTTGCCAT
TGCTACAGGCATCGTGGTGTCACGCTCGTCGTTTGGTATGGCTTCATTCAGCT
CCGGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCGCAG
TGTTATCACTCATGGTTATGGCAGCACTGCATAATTCTCTTACTGTCATGCCA
TCCGTAAGATGCTTTTCTGTGACTGGTGAGTACTCAACCAAGTCATTCTGAGA
ATAGTGTATGCGGCGACCGAGTTGCTCTTGCCCGGCGTCAATACGGGATAAT
ACCGCGCCACATAGCAGAACTTTAAAAGTGCTCATCATTGGAAAACGTTCTT
CGGGGCGAAAACTCTCAAGGATCTTACCGCTGTTGAGATCCAGTTCGATGTA
ACCCACTCGTGCACCCAACTGATCTTCAGCATCTTTTACTTTCACCAGCGTTT
CTGGGTGAGCAAAAACAGGAAGGCAAAATGCCGCAAAAAAGGGAATAAGGG
CGACACGGAAATGTTGAATACTCATACTCTTCCTTTTTCAATATTATTGAAGC
ATTTATCAGGGTTATTGTCTCATGAGCGGATACATATTTGAATGTATTTAGAA
AAATAAACAAATAGGGGTTCCGCGCACATTTCCCCGAAAAGTGCCACCTGAC
GTCTAAGAAACCATTATTATCATGACATTAACCTATAAAAATAGGCGTATCA
CGAGGCCCTTTCGTCTCGCGCGTTTCGGTGATGACGGTGAAAACCTCTGACAC
ATGCAGCTCCCGGAGACGGTCACAGCTTGTCTGTAAGCGGATGCCGGGAGCA
GACAAGCCCGTCAGGGCGCGTCAGCGGGTGTTGGCGGGTGTCGGGGCTGGCT
TAACTATGCGGCATCAGAGCAGATTGTACTGAGAGTGCACCATATGGACATA
TTGTCGTTAGAACGCGGCTACAATTAATACATAACCTTATGTATCATACACAT
ACGATTTAGGTGACACTATA
```
pRS306-Rpn10-FPR1:
```
TCGCGCGTTTCGGTGATGACGGTGAAAACCTCTGACACATGCAGCTCCCGGA      (SEQ ID NO:4)
GACGGTCACAGCTTGTCTGTAAGCGGATGCCGGGAGCAGACAAGCCCGTCAG
GGCGCGTCAGCGGGTGTTGGCGGGTGTCGGGGCTGGCTTAACTATGCGGCAT
CAGAGCAGATTGTACTGAGAGTGCACCACGCTTTTCAATTCAATTCATCATTT
TTTTTTTATTCTTTTTTTTTGATTTCGGTTTCTTTGAAATTTTTTTGATTCGGTAA
TCTCCGAACAGAAGGAAGAACGAAGGAAGGAGCACAGACTTAGATTGGTAT
ATATACGCATATGTAGTGTTGAAGAAACATGAAATTGCCCAGTATTCTTAACC
CAACTGCACAGAACAAAAACCTGCAGGAAACGAAGATAAATCATGTCGAAA
GCTACATATAAGGAACGTGCTGCTACTCATCCTAGTCCTGTTGCTGCCAAGCT
ATTTAATATCATGCACGAAAAGCAAACAAACTTGTGTGCTTCATTGGATGTTC
GTACCACCAAGGAATTACTGGAGTTAGTTGAAGCATTAGGTCCCAAAATTTG
TTTACTAAAAACACATGTGGATATCTTGACTGATTTTTCCATGGAGGGCACAG
```

-continued

```
TTAAGCCGCTAAAGGCATTATCCGCCAAGTACAATTTTTACTCTTCGAAGAC
AGAAAATTTGCTGACATTGGTAATACAGTCAAATTGCAGTACTCTGCGGGTG
TATACAGAATAGCAGAATGGGCAGACATTACGAATGCACACGGTGTGGTGGG
CCCAGGTATTGTTAGCGGTTTGAAGCAGGCGGCAGAAGAAGTAACAAAGGA
ACCTAGAGGCCTTTTGATGTTAGCAGAATTGTCATGCAAGGGCTCCCTATCTA
CTGGAGAATATACTAAGGGTACTGTTGACATTGCGAAGAGCGACAAAGATTT
TGTTATCGGCTTTATTGCTCAAAGAGACATGGGTGGAAGAGATGAAGGTTAC
GATTGGTTGATTATGACACCCGGTGTGGGTTTAGATGACAAGGGAGACGCAT
TGGGTCAACAGTATAGAACCGTGGATGATGTGGTCTCTACAGGATCTGACAT
TATTATTGTTGGAAGAGGACTATTTGCAAAGGGAAGGGATGCTAAGGTAGAG
GGTGAACGTTACAGAAAAGCAGGCTGGGAAGCATATTTGAGAAGATGCGGC
CAGCAAAACTAAAAAACTGTATTATAAGTAAATGCATGTATACTAAACTCAC
AAATTAGAGCTTCAATTTAATTATATCAGTTATTACCCTGCGGTGTGAAATAC
CGCACAGATGCGTAAGGAGAAAATACCGCATCAGGAAATTGTAAACGTTAAT
ATTTTGTTAAAATTCGCGTTAAATTTTTGTTAAATCAGCTCATTTTTTAACCAA
TAGGCCGAAATCGGCAAAATCCCTTATAAATCAAAAGAATAGACCGAGATAG
GGTTGAGTGTTGTTCCAGTTTGGAACAAGAGTCCACTATTAAAGAACGTGGA
CTCCAACGTCAAAGGGCGAAAAACCGTCTATCAGGGCGATGGCCCACTACGT
GAACCATCACCCTAATCAAGTTTTTTGGGGTCGAGGTGCCGTAAAGCACTAA
ATCGGAACCCTAAAGGGAGCCCCCGATTTAGAGCTTGACGGGGAAAGCCGG
CGAACGTGGCGAGAAAGGAAGGGAAGAAAGCGAAAGGAGCGGGCGCTAGG
GCGCTGGCAAGTGTAGCGGTCACGCTGCGCGTAACCACCACACCCGCCGCGC
TTAATGCGCCGCTACAGGGCGCGTCGCGCCATTCGCCATTCAGGCTGCGCAA
CTGTTGGGAAGGGCGATCGGTGCGGGCCTCTTCGCTATTACGCCAGCTGGCG
AAGGGGGGATGTGCTGCAAGGCGATTAAGTTGGGTAACGCCAGGGTTTTCCC
AGTCACGACGTTGTAAAACGACGGCCAGTGAATTGTAATACGACTCACTATA
GGGCGAATTGGAGCTCCACCGCGGTGGCGGCCGCAAAGGATTTTCGGTAAGC
GATATTCTAAAGAAGGACTACAAACAATTCAATTTCCAAGGAAAGGGACACA
AAGGGTTAGAGATTGGTCTTTCATCAATAGTAAAAAGAATGTCTTGGCTATTC
AATGAACACGGTGGTGAAGCAGATTTCGTCAACCAATGCAGAAGATTTCAGG
CGGAGAGGGGGCTCGATGTATTGGTTCTGTTGACTTCATGGAGGAAAGCTGG
TGATTCACACAGAGAATTGGTCATATTGGGAGACTCTAACGTGGTACGTGAA
CTCATTGAAAGGGTTAGCGACAAGCTCCAACTTCAATTATTTGGGGGCAATCT
TGATGGAGGTGTGGCGATGTTTAAGCAACTGAACGTCGAGGCCACCAGAAAG
CAAGTCGTCCCCTATTTAGAGGAAGCGTACTCAAACCTGGTTAATTAATTAGT
TGACCTTCAACAATTCGACGTCGAAAACCAAAGTACTGTTTGGTGGAATCAA
ACCTGGGAAACCACGTGGGCCATAAGCATATGGGCCAGGGATGGTTAACCTA
GCTTTTTCACCAACAGACAACTTTGGAATACCAACATCCCAACCCTTGATGAC
TTGGCCGACACCGATGTTACATTGGAATGGAGAGCCCCTGTCAACGGAGGAA
TCGAATTTTTGGCCGTTCTCCAAGGTACCGGTGTAATGAATGGTAACCAAGTC
ACCTGTCTTTGGGAAGGTGGCACCATCACCTGGGGAAATTCTGTCAATTTTGA
CGTTACCTTCAATTACTTCAGACGTACGGGAACTATGCATCTCTGAGGAATGG
TCTTCTCCTCCAACAAAACAGCATGCTTTGTCTTGGTGTTGTTCAGGCTGTTCA
GACTGCTCAGGCTGATCTTGTTGTTGTTGCTGCTGTCTTAACCTTTCCTGTCTT
TGCTGCTCTTCTTCCATAGACAGACGCAAGGCCATTGCCAGTTCTGGGTCCAT
TGATGGGTCTACCCCGAAGTCCATAAATGTGCCATTGGCATCGGAATCACCG
CCAGACCCACCAAAGGCGCCCATACCGGAGGATCCTTCTTCGAGAATTATGG
GTGAAGATGCGATGTTCTCGTACAGCAGTCTGGGGCCAGGCGTCACAGTAAG
CAAATGACTAGTTTCTTCTTGAGGGTTGTTCACTGCAGCTATGAACTCATCCA
AAAGCTCCGTGTTCTGTTCAATCTCTCCAAAATTGATGATGTCCACGGCAACA
TTATTCTTTTTCAGTGTTTTTGCCAATCTGATCAATTCGTCTTCTAGAACTAGT
GGATCCCCCGGGCTGCAGGAATTCGATATCAAGCTTATCGATACCGTCGACC
TCGAGGGGGGGCCCGGTACCCAGCTTTTGTTCCCTTTAGTGAGGGTTAATTCC
GAGCTTGGCGTAATCATGGTCATAGCTGTTTCCTGTGTGAAATTGTTATCCGC
TCACAATTCCACACAACATAGGAGCCGGAAGCATAAAGTGTAAAGCCTGGGG
TGCCTAATGAGTGAGGTAACTCACATTAATTGCGTTGCGCTCACTGCCCGCTT
TCCAGTCGGGAAACCTGTCGTGCCAGCTGCATTAATGAATCGGCCAACGCGC
GGGGAGAGGCGGTTTGCGTATTGGGCGCTCTTCCGCTTCCTCGCTCACTGACT
CGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGC
GTTTTTCCATAGGCTCGGCCCCCCTGACGAGCATCACAAAAATCGACGCTCA
AGTCAGAGGTGGCGAAACCCGACAGGACTATAAAGATACCAGGCGTTCCCCC
CTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCAATGCTCACGCTG
TAGGTATCTCAGTTCGGTGTAGGTCGTTCGCTCCAAGCTGGGCTGTGTGCACG
AACCCCCCGTTCAGCCCGACCGCTGCGCCTTATCCGGTAACTATCGTCTTGAG
TCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGCTGA
AGCCAGTTACCTTCGGAAAAAGAGTTGGTAGCTCTTGATCCGGCAAACAAAC
CACCGCTGGTAGCGGTGGTTTTTTTGTTTGCAAGCAGCAGATTACGCGCAGAA
AAAAAGGATCTCAAGAAGATCCTTTGATCTTTTCTACGGGGTCTGACGCTCAG
TGGAACGAAAACTCACGTTAAGGGATTTTGGTCATGAGATTATCAAAAAGGA
TCTTCACCTAGATCCTTTTAAATTAAAAATGAAGTTTTAAATCAATCTAAAGT
ATATATGAGTAAACTTGGTCTGACAGTTACCAATGCTTAATCAGTGAGGCAC
CTATCTCAGCGATCTGTCTATTTCGTTCATCCATAGTTGCCTGACTGCCCGTCG
TGTAGATAACTACGATACGGGAGGGCTTACCATCTGGCCCCAGTGCTGCAAT
GATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCA
```

-continued

```
TCCAGTCTATTAATTGTTGCCGGGAAGCTAGAGTAAGTAGTTCGCCAGTTAAT
AGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACAT
GATCCCCCATGTTGTGAAAAAAAGCGGTTAGCTCCTTCGGTCCTCCGATCGTT
GTCAGAAGTAAGTTGGCCGCAGTGTTATCACTCATGGTTATGGCAGCACTGC
ATAATTCTCTTACTGTCATGCCATCCGTAAGATGCTTTTCTGTGACTGGTGAG
TACTCAACCAAGTCATTCTGAGAATAGTGTATGCGGCGACCGAGTTGCTCTTG
CCCGGCGTCAATACGGGATAATACCGCGCCACATAGCAGAACTTTAAAAGTG
CTCATCATTGGAAAACGTTCTTCGGGGCGAAAACTCTCAAGGATCTTACCGCT
GTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGC
CGCAAAAAAGGGAATAAGGGCGACACGGAAATGTTGAATACTCATACTCTTC
CTTTTTCAATATTATTGAAGCATTTATCAGGGTTATTGTCTCATGAGCGGATA
CATATTTGAATGTATTTAGAAAAATAAACAAATAGGGGTTCCGCGCACATTT
CCCCGAAAAGTGCCACCTGACGTCTAAGAAACCATTATTATCATGACATTAA
CCTATAAAAATAGGCGTATCACGAGGCCCTTTCGTC
```

PROTet.e133-TOR-link-HIS3HA:
```
TCGAGTCCCTATCAGTGATAGAGATTGACATCCCTATCAGTGATAGAGATACT         (SEQ ID NO:5)
GAGCACATCAGCAGGACGCACTGACCGAATTCATTAAAGAGGAGAAAGGTA
CCCATGGGTCATAATCATAATCATAATCATAATCATAATCACAACGGTGGAG
ATGACGATGACAAGGTGGTCGACAAGCTTGGATCCATGATACATCAGCCAGA
TCCTACGGTGAGTAATTCCCTTTTGTCGTTGCTTTCTGATTTAGGGAAAGCTC
ATCCACAAGCTCTCGTGTATCCTTTAACTGTCGCGATCAAGTCTGAATCTGTT
TCAAGACAAAAAGCGGCTCTTTCAATAATAGAGAAAATTAGGATTCATAGTC
CAGTCCTGGTAAACCAGGCAGAATTAGTTAGTCACGAGTTGATCAGAGTAGC
CGTTCTATGGCACGAATTATGGTATGAAGGACTGGAAGATGCGAGCCGCCAA
TTTTTCGTTGAACATAACATAGAAAAAATGTTTTCTACTTTAGAACCTTTACA
TAAACACTTAGGCAATGAGCCTCAAACGTTAAGTGAGGTATCGTTTCAGAAA
TCATTTGGTAGAGATTTGAACGATGCCTACGAATGGTTGAATAACTACAAAA
AGTCAAAAGACATCAATAATTTGAACCAAGCTTGGGATATTTATTATAACGT
CTTCAGAAAAATAACACGTCAAATACCACAGTTACAAACCTTAGACTTACAG
CATGTTTCTCCCCAGCTTCTGGCTACTCATGATCTCGAATTGGCTGTTCCTCCT
AGGTGTTTTGTTGGAGGAGAAGACCATTCCTCAGAGATGCATAGTTCCCGTA
CGGGCGGCAGCGGCCGCACAGAGCAGAAAGCCCTAGTAAAGCGTATTACAA
ATGAAACCAAGATTCAGATTGCGATCTCTTTAAAGGGTGGTCCCCTAGCGAT
AGAGCACTCGATCTTCCCAGAAAAAGAGGCAGAAGCAGTAGCAGAACAGGC
CACACAATCGCAAGTGATTAACGTCCACACAGGTATAGGGTTTCTGGACCAT
ATGATACATGCTCTGGCCAAGCATTCCGGCTGGTCGCTAATCGTGAGTGCAT
TGGTGACTTACACATAGACGACCATCACACCACTGAAGACTGCGGGATTGCT
CTCGGTCAAGCTTTTAAAGAGGCCCTAGGGGCCGTGCGTGGAGTAAAAAGGT
TTGGATCAGGATTTGCGCCTTTGGATGAGGCACTTTCCAGAGCGGTGGTAGAT
CTTTCGAACAGGCCGTACGCAGTTGTCGAACTTGGTTTGCAAAGGGAGAAAG
TAGGAGATCTCTCTTGCGAGATGATCCCGCATTTTCTTGAAAGCTTTGCAGAG
GCTAGCAGAATTACCCTCCACGTTGATTGTCTGCGAGGCAAGAATGATCATC
ACCGTAGTGAGAGTGCGTTCAAGGCTCTTGCGGTTGCCATAAGAGAAGCCAC
CTCGCCCAATGGTACCAACGATGTTCCCTCCACCAAAGGTGTTCTTATGCTGC
AGTACCCATACGATGTTCCAGATTACGCTTAAGTCGACCTCGAGGTCATGTAA
TTAGTTATGTCACGCTTACATTCACGCCCTCCCCCCACATCCGCTCTAACCGA
AAAGGAAGGAGTTAGACAACCTGAAGTCTAGGTCCCTATTTATTTTTTTATAG
TTATGTTAGTATTAAGAACGTTATTTATATTTCAAATTTTTCTTTTTTTCTGTA
CAGACGCGTGTACGCATGTAACATTATACTGAAAACCTTGCTTGAGAAGGTT
TTGGGACGCTCGAAGGCTTTAATTTGCGGCCGGTACCGGTACCCAATTCGCCC
TATAGTGAGTCGTATTACGCGCGCTCACTGGCCGTCGTTTTACAACGTCGTGA
CTGGGAAAACCCTGGCGTTACCCAACTTAATCGCCTTGCAGCACATCCCCCTT
TCGCCAGCTGGCGTAATAGCGAAGAGGCCCGCACCGATCGATGCGGCCGCTT
AATTAATTAATCTAGAGGCATCAAATAAAACGAAAGGCTCAGTCGAAAGACT
GGGCCTTTCGTTTTATCTGTTGTTTGTCGGTGAACGCTCTCCTGAGTAGGACA
AATCCGCCGCCCTAGACCTAGGCGTTCGGCTGCGGCGAGCGGTATCAGCTCA
CTCAAAGGCGGTAATACGGTTATCCACAGAATCAGGGGATAACGCAGGAAA
GAACATGTGAGCAAAAGGCCAGCAAAAGGCCAGGAACCGTAAAAAGGCCGC
GTTGCTGGCGTTTTTCCATAGGCTCCGCCCCCTGACGAGCATCACAAAAATC
GACGCTCAAGTCAGAGGTGGCGAAACCCGACAGGACTATAAAGATACCAGG
CGTTTCCCCCTGGAAGCTCCCTCGTGCGCTCTCCTGTTCCGACCCTGCCGCTT
ACCGGATACCTGTCCGCCTTTCTCCCTTCGGGAAGCGTGGCGCTTTCTCAATG
CTCACGCTGTAGGTATCTCAGTTCGGTGTAGGTCGTTCGCTCCAAGCTGGGCT
```

```
-continued
GTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCA
CTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGC
GCTCTGCTGAAGCCAGTTACCTTCGGAAAAAGAGTTGGTAGCTCTTGATCCG
GCAAACAAACCACCGCTGGTAGCGGTGGTTTTTTGTTTGCAAGCAGCAGATT
ACGCGCAGAAAAAAAGGATCTCAAGAAGATCCTTTGATCTTTTCTACGGGGT
CTGACGCTCAGTGGAACGAAAACTCACGTTAAGGGATTTTGGTCATGACTAG
TGCTTGGATTCTCACCAATAAAAAACGCCCGGCGGCAACCGAGCGTTCTGAA
CAAATCCAGATGGAGTTCTGAGGTCATTACTGGATCTATCAACAGGAGTCCA
AGCGAGCTCGATATCAAATTACGCCCCGCCCTGCCACTCATCGCAGTACTGTT
GTAATTCATTAAGCATTCTGCCGACATGGAAGCCATCACAGACGGCATGATG
AACCTGAATCGCCAGCGGCATCAGCACCTTGTCGCCTTGCGTATAATATTTGC
CCATGGTGAAAACGGGGGCGAAGAAGTTGTCCATATTGGCCACGTTTAAATC
AAAACTGGTGAAACTCACCCAGGGATTGGCTGAGACGAAAAACATATTCTCA
ATAAACCCTTTAGGGAAATAGGCCAGGTTTTCACCGTAACACGCCACATCTT
GCGAATATATGTGTAGAAACTGCCGGAAATCGTCGTGGTATTCACTCCAGAG
CGATGAAAACGTTTCAGTTTGCTCATGGAAAACGGTGTAACAAGGGTGAACA
CTATCCCATATCACCAGCTCACCGTCTTTCATTGCCATACGAAATTCCGGATG
AGCATTCATCAGGCGGGCAAGAATGTGAATAAAGGCCGGATAAAACTTGTGC
TTATTTTTCTTTACGGTCTTTAAAAAGGCCGTAATATCCAGCTGAACGGTCTG
GTTATAGGTACATTGAGCAACTGACTGAAATGCCTCAAAATGTTCTTTACGAT
GCCATTGGGATATATCAACGGTGGTATATCCAGTGATTTTTTTCTCCATTTTA
GCTTCCTTAGCTCCTGAAAATCTCGATAACTCAAAAAATACGCCCGGTAGTG
ATCTTATTTCATTATGGTGAAAGTTGGAACCTCTTACGTGCCGATCAACGTCT
CATTTTCGCCAGATATCGACGTCTAAGAAACCATTATTATCATGACATTAACC
TATAAAAATAGGCGTATCACGAGGCCCTTTCGTCTTCACC
```

Primers

All primers used to construct the plasmids described above are set forth below. Construction of the $TOR_{S1972R}$ vectors used the same primers as the TOR vectors.

```
Primers for p415-TOR-HIS3
TOR-BamHI-L:          5'-cagcggggatccATGATACATCAGCCAGATCCTAC-3'              (SEQ ID NO:6)
TOR-XhoI-R:           5'-cagcgactcgagcAGGAACAGCCAATTCGAGAT-3'                 (SEQ ID NO:7)
HIS3-XhoI-L:          5'-caggtcctcgagccACAGAGCAGAAAGCCCTAGTA-3'               (SEQ ID NO:8)
HIS3-BamHI-R:         5'-catcgtggatccCTACATAAGAACACCTTTGGT-3'                 (SEQ ID NO:9)
Primers for p415-TOR-
link-HIS3HA
TOR-BamHI-L:          5'-cagcggggatccATGATACATCAGCCAGATCCTAC-3'              (SEQ ID NO:10)
tor-link-R-AvrII-BsiWI: 5'-cagaaccgtacgGGAACTATGCATCTCTGAGGAATGG TC          (SEQ ID NO:11)
                      TTCTCCTCCAACAAAACAcctaggAGGAACAGCCAATTCGAGAT-3'
HIS3-NotI-L:          5'-caggtcgcggccgcACAGAGCAGAAAGCCCTAGTA-3'              (SEQ ID NO:12)
HIS3-HA-R-PstI-SalI:  5'-cagaacgtcgacTTAAGCGTAATCTGGAACATCGTATGG             (SEQ ID NO:13)
                      GTA ctgcagCATAAGAACACCTTTGGTGGA-3'
BsiWI-NotI-L-II:      5'-gtacgGGCGGCagc-3'                                   (SEQ ID NO:14)
BsiWI-NotI-R-II:      5'-ggccgctGCCGCCc-3'                                   (SEQ ID NO:15)
Primers for pUG-spHIS5-
FPR1HA
FPR1-BsiWI-L:         5'-tcaactcgtacgTCTGAAGTAATTGAAGGTAACGT-3'              (SEQ ID NO:16)
FPR1-BamHI-R:         5'-cagcggggatccGTTGACCTTCAACAATTCGACGT-3'              (SEQ ID NO:17)
HAtag-BamHI-SalI-for: 5'-gatccTACCCATACGATGTTCCAGATTACGCTTAAg-3'             (SEQ ID NO:18)
HAtag-BamHI-SalI-rev: 5'-tcgacTTAAGCGTAATCTGGAACATCGTATGGGTAg-3'             (SEQ ID NO:19)
Primers for pRS306-Rpn10-
FPR1
Rpn10-ORF-L-XbaI:     5'-cagaactctagaAGACGAATTGATCAGATTGGC-3'                (SEQ ID NO:20)
Rpn10-ORF-R-SphI:     5'-cagaacgcatgcTTTGTCTTGGTGTTGTTCAGGCTGT-3'            (SEQ ID NO:21)
Rpn10-UTR-L-PacI:     5'-cagaacttaattaaCCAGGTTTGAGTACGCTTCC-3'               (SEQ ID NO:22)
Rpn10-UTR-R-NotI:     5'-cagaacgcggccgcAAAGGATTTTCGGTAAGCGA-3'               (SEQ ID NO:23)
FPR1-BsiWI-L:         5'-cagaaccgtacgTCTGAAGTAATTGAAGGTAACGT-3'              (SEQ ID NO:24)
FPR1-PacI-R:          5'-cagaacttaattaaTTAGTTGACCTTCAACAATTCGA-3'            (SEQ ID NO:25)
Linker-L-SphI:        5'-cTGTTTTGTTGGAGGAGAAGACCATTCCTCAGAGATGCAT            (SEQ ID NO:26)
                      AGTTCCc-3'
Linker-R-BsiWI-SphI:  5'-gtacgGGAACTATGCATCTCTGAGGAATGGTCTT                  (SEQ ID NO:27)
                      CTCCTCCAACAAAACAgtacg-3'
```

Primers for PROTet.e133-TOR-link-HIS3HA

No primers were used to create this construct. Instead, TOR-link-HIS3HA was excised from p415-TOR-link-HIS3HA using BamHI and PvuI, and then cloned into PROTet.e133.

EQUIVALENTS

Those skilled in the art will recognize, or be able to ascertain using no more than routine experimentation, many equivalents to the specific embodiments and methods described herein. Such equivalents are intended to be encompassed by the scope of the following claims. All publications and patent applications cited above are incorporated by reference in their entirety for all purposes to the same extent as if each individual publication or patent application were specifically and individually indicated to be so incorporated by reference.

What is claimed:

1. An in vitro method for targeted polypeptide degradation in a ubiquitin-independent manner comprising:
   a) providing a proteasome having a first member of a heterodimer pair covalently linked thereto;
   b) providing a target polypeptide having a second member of a heterodimer pair covalently linked thereto; and
   c) providing a heterodimerizer that binds the first member of the heterodimer pair and causes heterodimerization of the first member of the heterodimer pair and the second member of the heterodimer pair, such that the proteasome degrades the target polypeptide.

2. The method of claim 1, wherein said heterodimerizer is selected from the group consisting of FK-506, FK-506-cyclosporin A, an aptamer, coumermycin, bismethotrexate, dexamethasone-methotrexate, an RNA-protein binder, and a rapamycin derivative.

3. The method of claim 1, wherein said heterodimerizer comprises a first module that binds a proteasome and a second module that binds a target polypeptide.

4. The method of claim 3, wherein said first module is chemically crosslinked to said second module.

5. The method of claim 3, wherein said second module is an epitope tag or an antibody.

6. The method of claim 5, wherein said epitope tag is selected from the group consisting of hemagglutinin, c-myc and TAP.

7. An in vitro method for targeted polypeptide degradation in a ubiquitin-independent manner comprising:
   a) providing a proteasome comprising an Fpr1 tag;
   b) providing a target polypeptide comprising Tor; and
   c) providing rapamycin, such that binding of rapamycin to Tor forms a complex, said complex binding the proteasome comprising the Fpr1 tag, and such that the proteasome degrades the target polypeptide.

\* \* \* \* \*

SEQUENCE LISTING

<160> NUMBER OF SEQ ID NOS: 27

<210> SEQ ID NO 1
<211> LENGTH: 8977
<212> TYPE: DNA
<213> ORGANISM: Artificial Sequence
<220> FEATURE:
<223> OTHER INFORMATION: Plasmid p415-TOR-HIS3

<400> SEQUENCE: 1

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatcga ctacgtcgta aggccgtttc tgacagagta aaattcttga gggaactttc     240
accattatgg gaaatggttc aagaaggtat tgacttaaac tccatcaaat ggtcaggtca     300
ttgagtgttt tttatttgtt gtatttttt tttttagag aaaatcctcc aatatcaaat      360
taggaatcgt agtttcatga ttttctgtta cacctaactt tttgtgtggt gccctcctcc     420
ttgtcaatat taatgttaaa gtgcaattct ttttccttat cacgttgagc cattagtatc     480
aatttgctta cctgtattcc tttactatcc tcctttttct ccttcttgat aaatgtatgt     540
agattgcgta tatagtttcg tctaccctat gaacatattc cattttgtaa tttcgtgtcg     600
tttctattat gaatttcatt tataaagttt atgtacaaat atcataaaaa aagagaatct     660
ttttaagcaa ggattttctt aacttcttcg gcgacagcat caccgacttc ggtggtactg     720
ttggaaccac ctaaatcacc agttctgata cctgcatcca aaccttttt aactgcatct     780 tcaatggcct taccttcttc aggcaagttc aatgacaatt tcaacatcat gcagcagac      840 aagatagtgg cgatagggtc aaccttattc tttggcaaat ctggagcaga accgtggcat     900
ggttcgtaca aaccaaatgc ggtgttcttg tctggcaaag aggccaagga cgcagatggc     960
aacaaaccca aggaacctgg gataacggag gcttcatcgg agatgatatc accaaacatg    1020
ttgctggtga ttataatacc atttaggtgg gttgggttct taactaggat catggcggca    1080
gaatcaatca attgatgttg aaccttcaat gtagggaatt cgttcttgat ggtttcctcc    1140 acagttttc tccataatct tgaagaggcc aaaacattag ctttatccaa ggaccaaata    1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaatacctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttctttacgg attttagta aaccttgttc aggtctaaca    1500
ctaccggtac cccatttagg accacccaca gcacctaaca aaacggcatc aaccttcttg    1560
gaggcttcca gcgcctcatc tggaagtggg acacctgtag catcgatagc agcaccacca    1620
attaaatgat tttcgaaatc gaacttgaca ttggaacgaa catcagaaat agctttaaga    1680
accttaatgg cttcggctgt gatttcttga ccaacgtggt cacctggcaa acgacgatc      1740 ttcttagggg cagacatagg ggcagacatt agaatggtat atccttgaaa tatatatata    1800
tattgctgaa atgtaaaagg taagaaaagt tagaaagtaa gacgattgct aaccacctat    1860
tggaaaaaac aataggtcct taataatat tgtcaacttc aagtattgtg atgcaagcat    1920
ttagtcatga acgcttctct attctatatg aaaagccggt tccggcctct cacctttcct    1980
```

```
ttttctccca attttttcagt tgaaaaaggt atatgcgtca ggcgacctct gaaattaaca    2040
aaaaatttcc agtcatcgaa tttgattctg tgcgatagcg ccccgtgtgt ttctcgttat    2100
gttgaggaaa aaaataatgg ttgctaagag attcgaactc ttgcatctta cgatacctga    2160
gtattcccac agttaactgc ggtcaagata tttcttgaat caggcgcctt agaccgctcg    2220
gccaaacaac caattacttg ttgagaaata gagtataatt atcctataaa tataacgttt    2280
ttgaacacac atgaacaagg aagtacagga caattgattt tgaagagaat gtggattttg    2340
atgtaattgt tgggattcca tttttaataa ggcaataata ttaggtatgt ggatatacta    2400
gaagttctcc tcgaccgtcg atatgcggtg tgaaataccg cacagatgcg taaggagaaa    2460
ataccgcatc aggaaattgt aaacgttaat attttgttaa aattcgcgtt aaattttgt     2520
taaatcagct cattttttaa ccataggcc  gaaatcggca aaatccctta taaatcaaaa    2580
gaatagaccg atagggtt   gagtgttgtt ccagtttgga acaagagtcc actattaaag    2640
aacgtggact ccaacgtcaa agggcgaaaa accgtctatc agggcgatgg cccactacgt    2700
gaaccatcac cctaatcaag ttttttgggg tcgaggtgcc gtaaagcact aaatcggaac    2760
cctaaaggga gccccccgatt tagagcttga cggggaaagc cggcgaacgt ggcgagaaag    2820
gaagggaaga aagcgaaagg agcgggcgct agggcgctgg caagtgtagc ggtcacgctg    2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga aaggggatg  tgctgcaagg cgattaagtt gggtaacgcc agggttttcc    3060
cagtcacgac gttgtaaaac gacggccagt gagcgcgcgt aatacgactc actatagggc    3120
gaattgggta ccgtaccgg  ccgcaaatta aagccttcga gcgtcccaaa accttctcaa    3180
gcaaggtttt cagtataatg ttacatgcgt acacgcgtct gtacagaaaa aaagaaaaa    3240
tttgaaatat aaataacgtt cttaatacta acataactat aaaaaaataa atagggacct    3300
agacttcagg ttgtctaact ccttcctttt cggttagagc ggatgtgggg ggagggcgtg    3360
aatgtaagcg tgacataact aattacatga cctcgaggtc gacggtatcg ataagcttga    3420
tatcgaattc ctgcagcccg ggggatccct acataagaac cctttggtg  gagggaacat    3480
cgttggtacc attgggcgag gtggcttctc ttatggcaac cgcaagagcc ttgaacgcac    3540
tctcactacg gtgatgatca ttcttgcctc gcagacaatc aacgtggagg gtaattctgc    3600
tagcctctgc aaagctttca agaaaatgcg ggatcatctc gcaagagaga tctcctactt    3660
tctccctttg caaccaagt  tcgacaactg cgtacggcct gttcgaaaga tctaccaccg    3720
ctctggaaag tgcctcatcc aaaggcgcaa atcctgatcc aaacctttt  actccacgca    3780
cggcccctag ggcctcttta aaagcttgac cgagagcaat cccgcagtct tcagtggtgt    3840
gatggtcgtc tatgtgtaag tcaccaatgc actcaacgat tagcgaccag ccggaatgct    3900
tggccagagc atgtatcata tggtccagaa acccctatacc tgtgtggacg ttaatcactt    3960
gcgattgtgt ggcctgttct gctactgctt ctgcctcttt ttctgggaag atcgagtgct    4020
ctatcgctag gggaccaccc tttaaagaga tcgcaatctg aatcttggtt tcatttgtaa    4080
tacgctttac tagggctttc tgctctgtgg ctcgagcagg aacagccaat tcgagatcat    4140
gagtagccag aagctgggga gaaacatgct gtaagtctaa ggtttgtaac tgtgtatttt    4200
gacgtgttat ttttctgaag acgttataat aaatatccca agcttggttc aaattattga    4260
tgtcttttga cttttttgtag ttattcaacc attcgtaggc atcgttcaaa tctctaccaa    4320
```

```
atgatttctg aaacgatacc tcacttaacg tttgaggctc attgcctaag tgtttatgta    4380
aaggttctaa agtagaaaac atttttttcta tgttatgttc aacgaaaaat tggcggctcg    4440
catcttccag tccttcatac cataattcgt gccatagaac ggctactctg atcaactcgt    4500
gactaactaa ttctgcctgg tttaccagga ctggactatg aatcctaatt ttctctatta    4560
ttgaaagagc cgcttttttgt cttgaaacag attcagactt gatcgcgaca gttaaaggat    4620
acacgagagc ttgtggatga gctttcccta aatcagaaag caacgacaaa agggaattac    4680
tcaccgtagg atctggctga tgtatcatgg atccactagt tctagagcgg ccagcttgga    4740
gttgattgta tgcttggtat agcttgaaat attgtgcaga aaaagaaaca aggaagaaag    4800
ggaacgagaa caatgacgag gaaacaaaag attaataatt gcaggtctat ttatacttga    4860
tagcaaagcg gcaaactttt tttatttcaa attcaagtaa ctggaaggaa ggccgtatac    4920
cgttgctcat tagagagtag tgtgcgtgaa tgaaggaagg aaaaagtttc gtgtgttcga    4980
agatacccct catcagctct ggaacaacga catctgttgg tgctgtcttt gtcgttaatt    5040 ttttcctttta gtgtcttcca tcattttttt tgtcattgcg gatatggtga gacaacaacg    5100
ggggagagag aaaagaaaaa aaaagaaaag aagttgcatg cgcctattat tacttcaata    5160
gatggcaaat ggaaaaaggg tagtgaaact tcgatatgat gatggctatc aagtctaggg    5220
ctacagtatt agttcgttat gtaccaccat caatgaggca gtgtaattgg tgtagtcttg    5280
tttagcccat tatgtcttgt ctggtatctg ttctattgta tatctcccct ccgccaccta    5340
catgttaggg agaccaacga aggtattata ggaatcccga tgtatgggtt tggttgccag    5400
aaaagaggaa gtccatattg tacacccgga aacaacaaaa ggatatccga aatattccac    5460
ggtttagaaa aaaatcggaa aagagcgcgg aggggtgtta ccccccttct ctactagcat    5520
tggactttaa ttaatatatg tgcataggag aagtgtaaag ttcccttcca tattgtaaca    5580
taataaagtg cacacccaaa tgaattgaaa gcgtactcaa acagacaacc atttccagtg    5640
ttgtatgtac ctgtctattt atactggtag caaccctatt gctgtttcct cttcaaagta    5700
ctctagcggt tatgcgcgtc tcaccttcaa ggtcatggtc gctctattgt tcgcaccacc    5760
ggcaaactcg cgtctcgcaa gtcttggctc attcttctag tatactcatg ttgcaaatgc    5820
actcaggttc tttcggcaac ttaaataatg acaccagttg tcgtggtcgt catcatcgca    5880
accccaaccg gcattcttat tgcttctcca atctcgcccc ttagcgcagg gtaaaccttg    5940
gaaaatgcag gcgcaaaaaa ctccgccggg cacagcctca cgcccagcgt tatcgccggg    6000
ccggcaagag cgcgggtccg ccacagagtc agcatgattg tgcaattgcg taaactcgtt    6060
ttttcggcgc cgcaaagcca aatacatcat atcaacactt ttcactttat ttttcgttcg    6120
acccttatat ttgtcttttg ccttcatgct ccttgatttc ctatttcatt taccatcatt    6180
tcttgagctc cagcttttgt tccctttagt gagggttaat tgcgcgcttg gcgtaatcat    6240
ggtcatagct gtttcctgtg tgaattgtt atccgctcac aattccacac aacataggag    6300
ccggaagcat aaagtgtaaa gcctggggtg cctaatgagt gaggtaactc acattaattg    6360
cgttgcgctc actgcccgct ttccagtcgg gaaacctgtc gtgccagctg cattaatgaa    6420
tcggccaacg cgcggggaga ggcggtttgc gtattgggcg ctcttccgct tcctcgctca    6480
ctgactcgct gcgctcggtc gttcggctgc ggcgagcggt atcagctcac tcaaaggcgg    6540
taatacggtt atccacagaa tcaggggata acgcaggaaa gaacatgtga gcaaaaggcc    6600
agcaaaaggc caggaaccgt aaaaaggccg cgttgctggc gttttccat aggctccgcc    6660 cccctgacga gcatcacaaa aatcgacgct caagtcagag gtggcgaaac ccgacaggac    6720
```

```
tataaagata ccaggcgttt ccccctggaa gctccctcgt gcgctctcct gttccgaccc    6780
tgccgcttac cggatacctg tccgcctttc tcccttcggg aagcgtggcg ctttctcata    6840
gctcacgctg taggtatctc agttcggtgt aggtcgttcg ctccaagctg gctgtgtgc    6900 acgaaccccc cgttcagccc gaccgctgcg ccttatccgg taactatcgt cttgagtcca    6960
acccggtaag acacgactta tcgccactgg cagcagccac tggtaacagg attagcagag    7020
cgaggtatgt aggcggtgct acagagttct tgaagtggtg gcctaactac ggctacacta    7080
gaaggacagt atttggtatc tgcgctctgc tgaagccagt taccttcgga aaaagagttg    7140
gtagctcttg atccggcaaa caaccaccg ctggtagcgg tggttttttt gtttgcaagc     7200
agcagattac gcgcagaaaa aaaggatctc aagaagatcc tttgatcttt tctacggggt    7260
ctgacgctca gtggaacgaa aactcacgtt aagggatttt ggtcatgaga ttatcaaaaa    7320
ggatcttcac ctagatcctt ttaaattaaa aatgaagttt taaatcaatc taaagtatat    7380
atgagtaaac ttggtctgac agttaccaat gcttaatcag tgaggcacct atctcagcga    7440
tctgtctatt tcgttcatcc atagttgcct gactccccgt cgtgtagata actacgatac    7500
gggagggctt accatctggc cccagtgctg caatgatacc gcgagaccca cgctcaccgg    7560
ctccagattt atcagcaata aaccagccag ccggaagggc cgagcgcaga gtggtcctg     7620 caactttatc cgcctccatc cagtctatta attgttgccg ggaagctaga gtaagtagtt    7680
cgccagttaa tagtttgcgc aacgttgttg ccattgctac aggcatcgtg gtgtcacgct    7740
cgtcgtttgg tatggcttca ttcagctccg gttcccaacg atcaaggcga gttacatgat    7800
cccccatgtt gtgcaaaaaa gcggttagct ccttcggtcc tccgatcgtt gtcagaagta    7860
agttggccgc agtgttatca ctcatggtta tggcagcact gcataattct cttactgtca    7920
tgccatccgt aagatgcttt tctgtgactg gtgagtactc aaccaagtca ttctgagaat    7980
agtgtatgcg gcgaccgagt tgctcttgcc cggcgtcaat acgggataat accgcgccac    8040
atagcagaac tttaaaagtg ctcatcattg gaaaacgttc ttcggggcga aaactctcaa    8100
ggatcttacc gctgttgaga tccagttcga tgtaacccac tcgtgcaccc aactgatctt    8160
cagcatcttt tactttcacc agcgtttctg ggtgagcaaa acaggaagg caaaatgccg      8220 caaaaaaggg aataagggcg acacggaaat gttgaatact catactcttc cttttttcaat   8280 attattgaag catttatcag ggttattgtc tcatgagcgg atacatattt gaatgtattt    8340
agaaaaataa acaaataggg gttccgcgca catttccccg aaaagtgcca cctgggtcct    8400
tttcatcacg tgctataaaa ataattataa tttaaatttt ttaatataaa tatataaatt    8460
aaaaatagaa agtaaaaaaa gaattaaag aaaaaatagt ttttgttttc cgaagatgta     8520
aaagactcta gggggatcgc caacaaatac tacctttat cttgctcttc ctgctctcag     8580
gtattaatgc cgaattgttt catcttgtct gtgtagaaga ccacacacga aaatcctgtg    8640
attttacatt ttacttatcg ttaatcgaat gtatatctat ttaatctgct tttcttgtct    8700
aataaatata tatgtaaagt acgcttttg ttgaaatttt ttaaaccttt gtttattttt      8760
ttttcttcat tccgtaactc ttctaccttc tttatttact ttctaaaatc caaatacaaa    8820
acataaaaat aaataaacac agagtaaatt cccaaattat tccatcatta aaagatacga    8880
ggcgcgtgta agttacaggc aagcgatccg tcctaagaaa ccattattat catgacatta    8940
acctataaaa ataggcgtat cacgaggccc tttcgtc                             8977
```

<210> SEQ ID NO 2

<211> LENGTH: 9028
<212> TYPE: DNA
<213> ORGANISM: Artificial Sequence
<220> FEATURE:
<223> OTHER INFORMATION: Plasmid p415-TOR-link-HIS3HA

<400> SEQUENCE: 2

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatcga ctacgtcgta aggccgtttc tgacagagta aaattcttga gggaactttc     240
accattatgg gaaatggttc aagaaggtat tgacttaaac tccatcaaat ggtcaggtca     300
ttgagtgttt tttatttgtt gtattttttt tttttagag aaaatcctcc aatatcaaat     360
taggaatcgt agtttcatga ttttctgtta cacctaactt tttgtgtggt gccctcctcc     420
ttgtcaatat taatgttaaa gtgcaattct tttccttat cacgttgagc cattagtatc     480
aatttgctta cctgtattcc tttactatcc tccttttct ccttcttgat aaatgtatgt     540
agattgcgta tatagtttcg tctaccctat gaacatattc cattttgtaa tttcgtgtcg     600
tttctattat gaatttcatt tataaagttt atgtacaaat atcataaaaa aagagaatct     660
ttttaagcaa ggattttctt aacttcttcg gcgacagcat caccgacttc ggtggtactg     720
ttggaaccac ctaaatcacc agttctgata cctgcatcca aaacctttt aactgcatct     780
tcaatggcct taccttcttc aggcaagttc aatgacaatt tcaacatcat tgcagcagac     840
aagatagtgg cgatagggtc aaccttattc tttggcaaat ctggagcaga accgtggcat     900
ggttcgtaca aaccaaatgc ggtgttcttg tctggcaaag aggccaagga cgcagatggc     960
aacaaaccca aggaacctgg gataacggag gcttcatcgg agatgatatc accaaacatg    1020
ttgctggtga ttataatacc atttaggtgg gttgggttct taactaggat catggcggca    1080
gaatcaatca attgatgttg aaccttcaat gtagggaatt cgttcttgat ggtttcctcc    1140
acagttttc tccataatct tgaagaggcc aaaacattag ctttatccaa ggaccaaata    1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaataccctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttctttacgg attttagta aaccttgttc aggtctaaca    1500
ctaccggtac cccatttagg accacccaca gcacctaaca aaacggcatc aaccttcttg    1560
gaggcttcca gcgcctcatc tggaagtggg acacctgtag catcgatagc agcaccacca    1620
attaaatgat tttcgaaatc gaacttgaca ttggaacgaa catcagaaat agctttaaga    1680
accttaatgc cttcggctgt gatttcttga ccaacgtggt cacctggcaa aacgacgatc    1740
ttcttagggg cagacatagg ggcagacatt agaatggtat atccttgaaa tatatatata    1800
tattgctgaa atgtaaaagg taagaaaagt tagaaagtaa gacgattgct aaccacctat    1860
tggaaaaaac aataggtcct taaataatat tgtcaacttc aagtattgtg atgcaagcat    1920
ttagtcatga acgcttctct attctatatg aaaagccggt tccggcctct cacctttcct    1980
ttttctccca atttttcagt tgaaaaaggt atatgcgtca ggcgacctct gaaattaaca    2040
aaaaatttcc agtcatcgaa tttgattctg tgcgatagcg cccctgtgtg ttctcgttat    2100
gttgaggaaa aaaataatgg ttgctaagag attcgaactc ttgcatctta cgatacctga    2160
```

```
gtattcccac agttaactgc ggtcaagata tttcttgaat caggcgcctt agaccgctcg    2220
gccaaacaac caattacttg ttgagaaata gagtataatt atcctataaa tataacgttt    2280
ttgaacacac atgaacaagg aagtacagga caattgattt tgaagagaat gtggattttg    2340
atgtaattgt tgggattcca tttttaataa ggcaataata ttaggtatgt ggatatacta    2400
gaagttctcc tcgaccgtcg atatgcggtg tgaaataccg cacagatgcg taaggagaaa    2460
ataccgcatc aggaaattgt aaacgttaat attttgttaa aattcgcgtt aaattttttgt   2520 taaatcagct cattttttaa ccaataggcc gaaatcggca aaatccctta taaatcaaaa    2580
gaatagaccg agataggggt gagtgttgtt ccagtttgga acaagagtcc actattaaag    2640
aacgtggact ccaacgtcaa agggcgaaaa accgtctatc agggcgatgg cccactacgt    2700
gaaccatcac cctaatcaag ttttttgggg tcgaggtgcc gtaaagcact aaatcggaac    2760
cctaaaggga gccccccgatt tagagcttga cggggaaagc cggcgaacgt ggcgagaaag    2820
gaagggaaga agcgaaagg agcgggcgct agggcgctgg caagtgtagc ggtcacgctg     2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga aaggggggatg tgctgcaagg cgattaagtt gggtaacgcc agggttttcc    3060
cagtcacgac gttgtaaaac gacggccagt gagcgcgcgt aatacgactc actatagggc    3120
gaattgggta ccggtaccgg ccgcaaatta aagccttcga gcgtcccaaa accttctcaa    3180
gcaaggtttt cagtataatg ttacatgcgt acacgcgtct gtacagaaaa aaaagaaaaa    3240
tttgaaatat aaataacgtt cttaatacta acataactat aaaaaaataa atagggacct    3300
agacttcagg ttgtctaact ccttcctttt cggttagagc ggatgtgggg ggagggcgtg    3360
aatgtaagcg tgacataact aattacatga cctcgaggtc gacttaagcg taatctggaa    3420
catcgtatgg gtactgcagc ataagaacac ctttggtgga gggaacatcg ttggtaccat    3480
tgggcgaggt ggcttctctt atggcaaccg caagagcctt gaacgcactc tcactacggt    3540
gatgatcatt cttgcctcgc agacaatcaa cgtggagggt aattctgcta gcctctgcaa    3600
agctttcaag aaaatgcggg atcatctcgc aagagagatc tcctactttc tccctttgca    3660
aaccaagttc gacaactgcg tacggcctgt tcgaaagatc taccaccgct ctggaaagtg    3720
cctcatccaa aggcgcaaat cctgatccaa acctttttac tccacgcacg gcccctaggg    3780
cctctttaaa agcttgaccg agagcaatcc cgcagtcttc agtggtgtga tggtcgtcta    3840
tgtgtaagtc accaatgcac tcaacgatta gcgaccagcc ggaatgcttg ccagagcat    3900 gtatcatatg gtccagaaac cctatacctg tgtggacgtt aatcacttgc gattgtgtgg    3960
cctgttctgc tactgcttct gcctcttttt ctgggaagat cgagtgctct atcgctaggg    4020
gaccacccct taaagagatc gcaatctgaa tcttggtttc attttgtaata cgctttacta    4080 gggctttctg ctctgtgcgg ccgctgccgc ccgtacggga actatgcatc tctgaggaat    4140
ggtcttctcc tccaacaaaa cacctaggag gaacagccaa ttcgagatca tgagtagcca    4200
gaagctgggg agaaacatgc tgtaagtcta aggtttgtaa ctgtggtatt tgacgtgtta    4260 ttttttctgaa gacgttataa taaatatccc aagcttggtt caaattattg atgtcttttg    4320 acttttttgta gttattcaac cattcgtagg catcgttcaa atctctacca aatgattttct  4380 gaaacgatac ctcacttaac gtttgaggct cattgcctaa gtgttatgt aaaggttcta     4440 aagtagaaaa cattttttct atgttatgtt caacgaaaaa ttggcggctc gcatcttcca    4500
```

```
gtccttcata ccataattcg tgccatagaa cggctactct gatcaactcg tgactaacta    4560
attctgcctg gtttaccagg actggactat gaatcctaat tttctctatt attgaaagag    4620 ccgcttttg tcttgaaaca gattcagact tgatcgcgac agttaaagga tacacgagag    4680
cttgtggatg agctttccct aaatcagaaa gcaacgacaa aagggaatta ctcaccgtag    4740
gatctggctg atgtatcatg gatccactag ttctagagcg gccagcttgg agttgattgt    4800
atgcttggta tagcttgaaa tattgtgcag aaaaagaaac aaggaagaaa gggaacgaga    4860
acaatgacga ggaaacaaaa gattaataat tgcaggtcta tttatacttg atagcaaagc    4920
ggcaaacttt ttttatttca aattcaagta actggaagga aggccgtata ccgttgctca    4980
ttagagagta gtgtgcgtga atgaaggaag gaaaaagttt cgtgtgttcg aagatacccc    5040
tcatcagctc tggaacaacg acatctgttg gtgctgtctt tgtcgttaat ttttccttt    5100 agtgtcttcc atcatttttt ttgtcattgc ggatatggtg agacaacaac gggggagaga    5160
gaaaagaaaa aaaagaaaa gaagttgcat gcgcctatta ttacttcaat agatggcaaa    5220 tggaaaagg gtagtgaaac ttcgatatga tgatggctat caagtctagg gctacagtat    5280
tagttcgtta tgtaccacca tcaatgaggc agtgtaattg gtgtagtctt gtttagccca    5340
ttatgtcttg tctggtatct gttctattgt atatctcccc tccgccacct acatgttagg    5400
gagaccaacg aagtattat aggaatcccg atgtatgggt ttggttgcca gaaaagagga    5460
agtccatatt gtacacccgg aaacaacaaa aggatatccg aaatattcca cggtttagaa    5520
aaaaatcgga aaagagcgcg gaggggtgtt acccccttc tctactagca ttggactta    5580 attaatatat gtgcatagga gaagtgtaaa gttcccttcc atattgtaac ataataaagt    5640
gcacacccaa atgaattgaa agcgtactca aacagacaac catttccagt gttgtatgta    5700
cctgtctatt tatactggta gcaaccctat tgctgttcc tcttcaaagt actctagcgg    5760
ttatgcgcgt ctcaccttca aggtcatggt cgctctattg ttcgcaccac cggcaaactc    5820
gcgtctcgca agtcttggct cattcttcta gtatactcat gttgcaaatg cactcaggtt    5880
ctttcggcaa cttaaataat gacaccagtt gtcgtggtcg tcatcatcgc aaccccaacc    5940
ggcattctta ttgcttctcc aatctcgccc cttagcgcag ggtaaacctt ggaaaatgca    6000
ggcgcaaaaa actccgccgg gcacagcctc acgcccagcg ttatcgccgg ccggcaaga    6060 gcgcgggtcc gccacagagt cagcatgatt gtgcaattgc gtaaactcgt tttttcggcg    6120
ccgcaaagcc aaatacatca tatcaacact tttcacttta tttttcgttc gacccttata    6180
tttgtctttt gccttcatgc tccttgattt cctatttcat ttaccatcat ttcttgagct    6240
ccagcttttg ttcccttag tgagggttaa ttgcgcgctt ggcgtaatca tggtcatagc    6300
tgtttcctgt gtgaaattgt tatccgctca caattccaca caacatagga gccggaagca    6360
taaagtgtaa agcctggggt gcctaatgag tgaggtaact cacattaatt gcgttgcgct    6420
cactgcccgc tttccagtcg ggaaacctgt cgtgccagct gcattaatga atcggccaac    6480
gcgcggggag aggcggtttg cgtattgggc gctcttccgc ttcctcgctc actgactcgc    6540
tgcgctcggt cgttcggctg cggcgagcgg tatcagctca ctcaaaggcg gtaatacggt    6600
tatccacaga atcaggggat aacgcaggaa agaacatgtg agcaaaaggc cagcaaaagg    6660
ccaggaaccg taaaaaggcc gcgttgctgg cgttttttcca taggctccgc cccctgacg    6720 agcatcacaa aaatcgacgc tcaagtcaga ggtggcgaaa cccgacagga ctataaagat    6780
accaggcgtt tcccctggaa gctccctcg tgcgctctcc tgttccgacc ctgccgctta    6840
ccggatacct gtccgccttt ctcccttcgg gaagcgtggc gctttctcat agctcacgct    6900
```

```
gtaggtatct cagttcggtg taggtcgttc gctccaagct gggctgtgtg cacgaacccc    6960
ccgttcagcc cgaccgctgc gccttatccg gtaactatcg tcttgagtcc aacccggtaa    7020
gacacgactt atcgccactg gcagcagcca ctggtaacag gattagcaga gcgaggtatg    7080
taggcggtgc tacagagttc ttgaagtggt ggcctaacta cggctacact agaaggacag    7140
tatttggtat ctgcgctctg ctgaagccag ttaccttcgg aaaaagagtt ggtagctctt    7200
gatccggcaa acaaaccacc gctggtagcg gtggtttttt tgtttgcaag cagcagatta    7260
cgcgcagaaa aaaaggatct caagaagatc ctttgatctt ttctacgggg tctgacgctc    7320
agtggaacga aaactcacgt taagggattt tggtcatgag attatcaaaa aggatcttca    7380
cctagatcct tttaaattaa aaatgaagtt ttaaatcaat ctaaagtata tatgagtaaa    7440
cttggtctga cagttaccaa tgcttaatca gtgaggcacc tatctcagcg atctgtctat    7500
ttcgttcatc catagttgcc tgactccccg tcgtgtagat aactacgata cgggagggct    7560
taccatctgg ccccagtgct gcaatgatac cgcgagaccc acgctcaccg gctccagatt    7620
tatcagcaat aaaccagcca gccggaaggg ccgagcgcag aagtggtcct gcaactttat    7680
ccgcctccat ccagtctatt aattgttgcc gggaagctag agtaagtagt tcgccagtta    7740
atagtttgcg caacgttgtt gccattgcta caggcatcgt ggtgtcacgc tcgtcgtttg    7800
gtatggcttc attcagctcc ggttcccaac gatcaaggcg agttacatga tcccccatgt    7860
tgtgcaaaaa agcggttagc tccttcggtc ctccgatcgt tgtcagaagt aagttggccg    7920
cagtgttatc actcatggtt atggcagcac tgcataattc tcttactgtc atgccatccg    7980
taagatgctt ttctgtgact ggtgagtact caaccaagtc attctgagaa tagtgtatgc    8040
ggcgaccgag ttgctcttgc ccggcgtcaa tacgggataa taccgcgcca catagcagaa    8100
ctttaaaagt gctcatcatt ggaaaacgtt cttcggggcg aaaactctca aggatcttac    8160
cgctgttgag atccagttcg atgtaaccca ctcgtgcacc caactgatct tcagcatctt    8220
ttactttcac cagcgtttct gggtgagcaa aaacaggaag gcaaaatgcc gcaaaaaagg    8280
gaataagggc gacacggaaa tgttgaatac tcatactctt cctttttcaa tattattgaa    8340
gcatttatca gggttattgt ctcatgagcg gatacatatt tgaatgtatt tagaaaaata    8400
aacaaatagg ggttccgcgc acatttcccc gaaaagtgcc acctgggtcc ttttcatcac    8460
gtgctataaa aataattata atttaaattt tttaatataa atatataaat taaaaataga    8520
aagtaaaaaa agaaattaaa gaaaaaatag ttttgttttt ccgaagatgt aaaagactct    8580
aggggggatcg ccaacaaata ctacctttta tcttgctctt cctgctctca ggtattaatg    8640
ccgaattgtt tcatcttgtc tgtgtagaag accacacacg aaaatcctgt gattttacat    8700
tttacttatc gttaatcgaa tgtatatcta tttaatctgc ttttcttgtc taataaatat    8760
atatgtaaag tacgcttttt gttgaaattt tttaaacctt tgtttatttt tttttcttca    8820
ttccgtaact cttctacctt ctttatttac tttctaaaat ccaaatacaa aacataaaaa    8880
taaataaaca cagagtaaat tcccaaatta ttccatcatt aaaagatacg aggcgcgtgt    8940
aagttacagg caagcgatcc gtcctaagaa accattatta tcatgacatt aacctataaa    9000
aataggcgta tcacgaggcc ctttcgtc                                       9028
```

<210> SEQ ID NO 3
<211> LENGTH: 4219
<212> TYPE: DNA
<213> ORGANISM: Artificial Sequence
<220> FEATURE:

<223> OTHER INFORMATION: Plasmid pUG-spHIS5-FPR1HA

<400> SEQUENCE: 3

```
gaacgcggcc gccagctgaa gcttcgtacg tctgaagtaa ttgaaggtaa cgtcaaaatt      60
gacagaattt ccccaggtga tggtgccacc ttcccaaaga caggtgactt ggttaccatt     120
cattacaccg gtaccttgga gaacggccaa aaattcgatt cctccgttga caggggctct     180
ccattccaat gtaacatcgg tgtcggccaa gtcatcaagg gttgggatgt tggtattcca     240
aagttgtctg ttggtgaaaa agctaggtta accatccctg cccatatgc ttatggccca     300
cgtggtttcc caggtttgat tccaccaaac agtactttgg ttttcgacgt cgaattgttg     360
aaggtcaacg gatcctaccc atacgatgtt ccagattacg cttaagtcga caacccttaa     420
tataacttcg tataatgtat gctatacgaa gttattaggt ctagagatct gtttagcttg     480
cctcgtcccc gccgggtcac ccggccagcg acatggaggc ccagaatacc ctccttgaca     540
gtcttgacgt gcgcagctca ggggcatgat gtgactgtcg cccgtacatt tagcccatac     600
atccccatgt ataatcattt gcatccatac attttgatgg ccgcacggcg cgaagcaaaa     660
attacggctc ctcgctgcag acctgcgagc agggaaacgc tccccctcaca gacgcgttga    720
attgtcccca cgccgcgccc ctgtagagaa atataaaagg ttaggatttg ccactgaggt     780
tcttctttca tatacttcct tttaaaatct tgctaggata cagttctcac atcacatccg     840
aacataaaca accatgggta ggagggcttt tgtagaaaga aatacgaacg aaacgaaaat     900
cagcgttgcc atcgctttgg acaaagctcc cttacctgaa gagtcgaatt ttattgatga     960
acttataact tccaagcatg caaaccaaaa gggagaacaa gtaatccaag tagacacggg    1020
aattggattc ttggatcaca tgtatcatgc actggctaaa catgcaggct ggagcttacg    1080
actttactca agaggtgatt taatcatcga tgatcatcac actgcagaag atactgctat    1140
tgcacttggt attgcattca agcaggctat gggtaacttt gccggcgtta aaagatttgg    1200
acatgcttat tgtccacttg acgaagctct ttctagaagc gtagttgact gtcgggacg     1260
gccctatgct gttatcgatt tgggattaaa gcgtgaaaag gttggggaat tgtcctgtga    1320
aatgatccct cacttactat attccttttc ggtagcagct ggaattactt tgcatgttac    1380
ctgcttatat ggtagtaatg accatcatcg tgctgaaagc gcttttaaat ctctggctgt    1440
tgccatgcgc gcggctacta gtcttactgg aagttctgaa gtcccaagca cgaagggagt    1500
gttgtaaaga gtactgacaa taaaaagatt cttgttttca agaacttgtc atttgtatag    1560
tttttttata ttgtagttgt tctattttaa tcaaatgtta gcgtgattta tattttttt     1620
cgcctcgaca tcatctgccc agatgcgaag ttaagtgcgc agaaagtaat atcatgcgtc    1680
aatcgtatgt gaatgctggt cgctatactg ctgtcgattc gatactaacg ccgccatcca    1740
gtttaaacga gctctcgaga acccttaata taacttcgta taatgtatgc tatacgaagt    1800
tattaggtga tatcagatcc actagtggcc tatgcggccg cggatctgcc ggtctcccta    1860
tagtgagtcg tattaatttc gataagccag gttaacctgc attaatgaat cggccaacgc    1920
gcggggagag gcggtttgcg tattgggcgc tcttccgctt cctcgctcac tgactcgctg    1980
cgctcggtcg ttcggctgcg gcgagcggta tcagctcact caaaggcggt aatacggtta    2040
tccacagaat caggggataa cgcaggaaag aacatgtgag caaaaggcca gcaaaggcc    2100
aggaaccgta aaaaggccgc gttgctggcg ttttccata ggctccgccc cctgacgag     2160
catcacaaaa atcgacgctc aagtcagagg tggcgaaacc cgacaggact ataaagatac    2220
caggcgtttc ccctggaag ctccctcgtg cgctctcctg ttccgaccct gccgcttacc     2280
```

```
ggatacctgt ccgcctttct cccttcggga agcgtggcgc tttctcaatg ctcacgctgt    2340
aggtatctca gttcggtgta ggtcgttcgc tccaagctgg gctgtgtgca cgaaccccccc   2400 gttcagcccg accgctgcgc cttatccggt aactatcgtc ttgagtccaa cccggtaaga   2460
cacgacttat cgccactggc agcagccact ggtaacagga ttagcagagc gaggtatgta   2520
ggcggtgcta cagagttctt gaagtggtgg cctaactacg gctacactag aaggacagta   2580
tttggtatct gcgctctgct gaagccagtt accttcggaa aaagagttgg tagctcttga   2640
tccggcaaac aaaccaccgc tggtagcggt ggttttttg tttgcaagca gcagattacg     2700
cgcagaaaaa aaggatctca agaagatcct ttgatctttt ctacggggtc tgacgctcag   2760
tggaacgaaa actcacgtta agggattttg gtcatgagat tatcaaaaag gatcttcacc   2820
tagatccttt taaattaaaa atgaagtttt aaatcaatct aaagtatata tgagtaaact   2880
tggtctgaca gttaccaatg cttaatcagt gaggcaccta tctcagcgat ctgtctattt   2940
cgttcatcca tagttgcctg actccccgtc gtgtagataa ctacgatacg ggagggctta   3000
ccatctggcc ccagtgctgc aatgataccg cgagacccac gctcaccggc tccagattta   3060
tcagcaataa accagccagc cggaagggcc gagcgcagaa gtggtcctgc aactttatcc   3120
gcctccatcc agtctattaa ttgttgccgg gaagctagag taagtagttc gccagttaat   3180
agtttgcgca acgttgttgc cattgctaca ggcatcgtgg tgtcacgctc gtcgtttggt   3240
atggcttcat tcagctccgg ttcccaacga tcaaggcgag ttacatgatc ccccatgttg   3300
tgcaaaaaag cggttagctc cttcggtcct ccgatcgttg tcagaagtaa gttggccgca   3360
gtgttatcac tcatggttat ggcagcactg cataattctc ttactgtcat gccatccgta   3420
agatgctttt ctgtgactgg tgagtactca accaagtcat tctgagaata gtgtatgcgg   3480
cgaccgagtt gctcttgccc ggcgtcaata cgggataata ccgcgccaca tagcagaact   3540
ttaaaagtgc tcatcattgg aaaacgttct cggggcgaaa actctcaag gatcttaccg   3600 ctgttgagat ccagttcgat gtaacccact cgtgcaccca actgatcttc agcatctttt   3660
actttcacca gcgtttctgg gtgagcaaaa acaggaaggc aaaatgccgc aaaaaaggga   3720
ataagggcga cacggaaatg ttgaatactc atactcttcc ttttttcaata ttattgaagc   3780 atttatcagg gttattgtct catgagcgga tacatatttg aatgtattta gaaaaataaa   3840
caaatagggg ttccgcgcac atttccccga aaagtgccac ctgacgtcta agaaaccatt   3900
attatcatga cattaaccta taaaaatagg cgtatcacga ggccctttcg tctcgcgcgt   3960
ttcggtgatg acggtgaaaa cctctgacac atgcagctcc cggagacggt cacagcttgt   4020
ctgtaagcgg atgccgggag cagacaagcc cgtcagggcg cgtcagcggg tgttggcggg   4080
tgtcggggct ggcttaacta tgcggcatca gagcagattg tactgagagt gcaccatatg   4140
gacatattgt cgttagaacg cggctacaat taatacataa ccttatgtat catacacata   4200
cgatttaggt gacactata                                                 4219

<210> SEQ ID NO 4
<211> LENGTH: 5643
<212> TYPE: DNA
<213> ORGANISM: Artificial Sequence
<220> FEATURE:
<223> OTHER INFORMATION: Plasmid pRS306-Rpn10-FPR1

<400> SEQUENCE: 4
tcgcgcgttt cggtgatgac ggtgaaaacc tctgacacat gcagctcccg gagacggtca       60
```

```
cagcttgtct gtaagcggat gccgggagca gacaagcccg tcaggcgcg tcagcgggtg      120 ttggcgggtg tcgggctgg cttaactatg cggcatcaga gcagattgta ctgagagtgc      180
accacgcttt tcaattcaat tcatcatttt ttttttattc tttttttga tttcggtttc      240 tttgaaattt ttttgattcg gtaatctccg aacagaagga agaacgaagg aaggagcaca     300
gacttagatt ggtatatata cgcatatgta gtgttgaaga acatgaaat tgcccagtat      360 tcttaaccca actgcacaga acaaaaacct gcaggaaacg aagataaatc atgtcgaaag     420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga tttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta caaaggaac     840 ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag gaagggatg    1140 ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta    1380 aattttttgtt aaatcagctc attttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt ttttggggt cgaggtgccg taaagcacta    1620
aatcggaacc ctaaagggag ccccgatt agagcttgac ggggaaagcc ggcgaacgtg     1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcca ccgcggtggc ggccgcaaag gatttcggt aagcgatatt    2040 ctaaagaagg actacaaaca attcaatttc caaggaaagg gacacaaagg gttagagatt   2100
ggtctttcat caatagtaaa aagaatgtct tggctattca atgaacacgg tggtgaagca   2160
gatttcgtca accaatgcag aagatttcag gcggagaggg ggctcgatgt attggttctg   2220
ttgacttcat ggaggaaagc tggtgattca cacagagaat tggtcatatt gggagactct   2280
aacgtggtac gtgaactcat tgaaagggtt agcgacaagc tccaacttca attatttggg   2340
ggcaatcttg atgaggtgt ggcgatgttt aagcaactga acgtcgaggc caccagaaag    2400
caagtcgtcc cctatttaga ggaagcgtac tcaaacctgg ttaattaatt agttgacctt   2460
```

```
caacaattcg acgtcgaaaa ccaaagtact gtttggtgga atcaaacctg ggaaaccacg    2520
tgggccataa gcatatgggc cagggatggt taacctagct ttttcaccaa cagacaactt    2580
tggaatacca acatcccaac ccttgatgac ttggccgaca ccgatgttac attggaatgg    2640
agagcccctg tcaacggagg aatcgaattt ttggccgttc tccaaggtac cggtgtaatg    2700
aatggtaacc aagtcacctg tctttgggaa ggtggcacca tcacctgggg aaattctgtc    2760
aattttgacg ttaccttcaa ttacttcaga cgtacgggaa ctatgcatct ctgaggaatg    2820
gtcttctcct ccaacaaaac agcatgcttt gtcttggtgt tgttcaggct gttcagactg    2880
ctcaggctga tcttgttgtt gttgctgctg tcttaacctt tcctgtcttt gctgctcttc    2940
ttccatagac agacgcaagg ccattgccag ttctgggtcc attgatgggt ctaccccgaa    3000
gtccataaat gtgccattgg catcggaatc accgccagac ccaccaaagg cgcccatacc    3060
ggaggatcct tcttcgagaa ttatgggtga agatgcgatg ttctcgtaca gcagtctggg    3120
gccaggcgtc acagtaagca aatgactagt ttcttcttga gggttgttca ctgcagctat    3180
gaactcatcc aaaagctccg tgttctgttc aatctctcca aaattgatga tgtccacggc    3240
aacattattc ttttttcagtg ttttttgccaa tctgatcaat tcgtcttcta gaactagtgg    3300
atcccccggg ctgcaggaat tcgatatcaa gcttatcgat accgtcgacc tcgaggggg    3360 gcccggtacc cagcttttgt tccctttagt gagggttaat tccgagcttg gcgtaatcat    3420
ggtcatagct gtttcctgtg tgaaattgtt atccgctcac aattccacac aacataggag    3480
ccggaagcat aaagtgtaaa gcctggggtg cctaatgagt gaggtaactc acattaattg    3540
cgttgcgctc actgcccgct ttccagtcgg gaaacctgtc gtgccagctg cattaatgaa    3600
tcggccaacg cgcggggaga ggcggtttgc gtattgggcg ctcttccgct tcctcgctca    3660
ctgactcgct gcgctcggtc gttcggctgc ggcgagcggt atcagctcac tcaaaggcgg    3720
taatacggtt atccacagaa tcaggggata acgcaggaaa gaacatgtga gcaaaaggcc    3780
agcaaaaggc caggaaccgt aaaaaggccg cgttgctggc gttttttccat aggctcggcc    3840 cccctgacga gcatcacaaa aatcgacgct caagtcagag gtggcgaaac ccgacaggac    3900
tataaagata ccaggcgttc ccccctggaa gctccctcgt gcgctctcct gttccgaccc    3960
tgccgcttac cggatacctg tccgcctttc tcccttcggg aagcgtggcg ctttctcaat    4020
gctcacgctg taggtatctc agttcggtgt aggtcgttcg ctccaagctg ggctgtgtgc    4080
acgaaccccc cgttcagccc gaccgctgcg ccttatccgg taactatcgt cttgagtcca    4140
acccggtaag acacgactta tcgccactgg cagcagccac tggtaacagg attagcagag    4200
cgaggtatgt aggcggtgct acagagttct tgaagtggtg gcctaactac ggctacacta    4260
gaaggacagt atttggtatc tgcgctctgc tgaagccagt taccttcgga aaaagagttg    4320
gtagctcttg atccggcaaa caaaccaccg ctggtagcgg tggttttttt gtttgcaagc    4380
agcagattac gcgcagaaaa aaaggatctc aagaagatcc tttgatcttt tctacggggt    4440
ctgacgctca gtggaacgaa aactcacgtt aagggatttt ggtcatgaga ttatcaaaaa    4500
ggatcttcac ctagatcctt ttaaattaaa aatgaagttt taaatcaatc taaagtatat    4560
atgagtaaac ttggtctgac agttaccaat gcttaatcag tgaggcacct atctcagcga    4620
tctgtctatt tcgttcatcc atagttgcct gactgcccgt cgtgtagata actacgatac    4680
gggagggctt accatctggc cccagtgctg caatgatacc gcgagaccca cgctcaccgg    4740
ctccagattt atcagcaata aaccagccag ccggaagggc cgagcgcaga agtggtcctg    4800
```

-continued

```
caactttatc cgcctccatc cagtctatta attgttgccg ggaagctaga gtaagtagtt    4860
cgccagttaa tagtttgcgc aacgttgttg ccattgctac aggcatcgtg gtgtcacgct    4920
cgtcgtttgg tatggcttca ttcagctccg gttcccaacg atcaaggcga gttacatgat    4980
cccccatgtt gtgaaaaaaa gcggttagct ccttcggtcc tccgatcgtt gtcagaagta    5040
agttggccgc agtgttatca ctcatggtta tggcagcact gcataattct cttactgtca    5100
tgccatccgt aagatgcttt tctgtgactg gtgagtactc aaccaagtca ttctgagaat    5160
agtgtatgcg cgaccgagt tgctcttgcc cggcgtcaat acgggataat accgcgccac    5220
atagcagaac tttaaaagtg ctcatcattg gaaaacgttc ttcggggcga aaactctcaa    5280
ggatcttacc gctgttgaga tccagttcga tgtaacccac tcgtgcaccc aactgatctt    5340
cagcatcttt tactttcacc agcgtttctg ggtgagcaaa acaggaagg caaaatgccg    5400 caaaaaggg aataagggcg acacggaaat gttgaatact catactcttc cttttttcaat    5460 attattgaag catttatcag ggttattgtc tcatgagcgg atacatattt gaatgtattt    5520
agaaaaataa acaaataggg gttccgcgca catttccccg aaaagtgcca cctgacgtct    5580
aagaaaccat tattatcatg acattaacct ataaaaatag gcgtatcacg aggccctttc    5640
gtc                                                                 5643

<210> SEQ ID NO 5
<211> LENGTH: 3916
<212> TYPE: DNA
<213> ORGANISM: Artificial Sequence
<220> FEATURE:
<223> OTHER INFORMATION: Plasmid PROTet.e133-TOR-link-HIS3HA

<400> SEQUENCE: 5
tcgagtccct atcagtgata gagattgaca tccctatcag tgatagagat actgagcaca      60
tcagcaggac gcactgaccg aattcattaa agaggagaaa ggtacccatg ggtcataatc     120
ataatcataa tcataatcat aatcacaacg gtggagatga cgatgacaag gtggtcgaca     180
agcttggatc catgatacat cagccagatc ctacggtgag taattccctt ttgtcgttgc     240
tttctgattt agggaaagct catccacaag ctctcgtgta tcctttaact gtcgcgatca     300
agtctgaatc tgtttcaaga caaaaagcgg ctctttcaat aatagagaaa attaggattc     360
atagtccagt cctggtaaac caggcagaat tagttagtca cgagttgatc agagtagccg     420
ttctatggca cgaattatgg tatgaaggac tggaagatgc gagccgccaa ttttcgttg     480 aacataacat agaaaaatg ttttctactt tagaaccttt acataaacac ttaggcaatg     540
agcctcaaac gttaagtgag gtatcgtttc agaaatcatt tggtagagat ttgaacgatg     600
cctacgaatg gttgaataac tacaaaaagt caaaagacat caataatttg aaccaagctt     660
gggatattta ttataacgtc ttcagaaaaa taacacgtca ataccacag ttacaaaccct     720 tagacttaca gcatgtttct ccccagcttc tggctactca tgatctcgaa ttggctgttc     780
ctcctaggtg ttttgttgga ggagaagacc attcctcaga gatgcatagt tcccgtacgg     840
gcggcagcgc ccgcacagag cagaaagccc tagtaaagcg tattacaaat gaaaccaaga     900
ttcagattgc gatctcttta aagggtggtc cctagcgat agagcactcg atcttcccag     960
aaaaagaggc agaagcagta gcagaacagg ccacacaatc gcaagtgatt aacgtccaca    1020
caggtatagg gtttctggac catatgatac atgctctggc caagcattcc ggctggtcgc    1080
taatcgttga gtgcattggt gacttacaca tagacgacca tcacaccact gaagactgcg    1140
ggattgctct cggtcaagct tttaaagagg ccctagggg cgtgcgtgga gtaaaaggt    1200
```

```
ttggatcagg atttgcgcct ttggatgagg cactttccag agcggtggta gatctttcga   1260
acaggccgta cgcagttgtc gaacttggtt tgcaaaggga gaaagtagga gatctctctt   1320
gcgagatgat cccgcatttt cttgaaagct ttgcagaggc tagcagaatt accctccacg   1380
ttgattgtct gcgaggcaag aatgatcatc accgtagtga gagtgcgttc aaggctcttg   1440
cggttgccat aagagaagcc acctcgccca atggtaccaa cgatgttccc tccaccaaag   1500
gtgttcttat gctgcagtac ccatacgatg ttccagatta cgcttaagtc gacctcgagg   1560
tcatgtaatt agttatgtca cgcttacatt cacgccctcc ccccacatcc gctctaaccg   1620
aaaaggaagg agttagacaa cctgaagtct aggtccctat ttattttttt atagttatgt   1680
tagtattaag aacgttattt atatttcaaa ttttctttt ttttctgtac agacgcgtgt   1740
acgcatgtaa cattatactg aaaaccttgc ttgagaaggt tttgggacgc tcgaaggctt   1800
taatttgcgg ccggtaccgg tacccaattc gccctatagt gagtcgtatt acgcgcgctc   1860
actggccgtc gttttacaac gtcgtgactg ggaaaaccct ggcgttaccc aacttaatcg   1920
ccttgcagca catccccctt cgccagctg gcgtaatagc gaagaggccc gcaccgatcg   1980
atgcggccgc ttaattaatt aatctagagg catcaaataa aacgaaaggc tcagtcgaaa   2040
gactgggcct ttcgttttat ctgttgtttg tcggtgaacg ctctcctgag taggacaaat   2100
ccgccgccct agacctaggc gttcggctgc ggcgagcggt atcagctcac tcaaaggcgg   2160
taatacggtt atccacagaa tcaggggata acgcaggaaa gaacatgtga gcaaaaggcc   2220
agcaaaaggc caggaaccgt aaaaaggccg cgttgctggc gttttccat aggctccgcc   2280 cccctgacga gcatcacaaa aatcgacgct caagtcagag gtggcgaaac ccgacaggac   2340
tataaagata ccaggcgttt ccccctggaa gctccctcgt gcgctctcct gttccgaccc   2400
tgccgcttac cggatacctg tccgcctttc tcccttcggg aagcgtggcg ctttctcaat   2460
gctcacgctg taggtatctc agttcggtgt aggtcgttcg ctccaagctg ggctgtgtgc   2520
acgaaccccc cgttcagccc gaccgctgcg ccttatccgg taactatcgt cttgagtcca   2580
acccggtaag acacgactta tcgccactgg cagcagccac tggtaacagg attagcagag   2640
cgaggtatgt aggcggtgct acagagttct tgaagtggtg gcctaactac ggctacacta   2700
gaaggacagt atttggtatc tgcgctctgc tgaagccagt taccttcgga aaaagagttg   2760
gtagctcttg atccggcaaa caaaccaccg ctggtagcgg tggtttttt gtttgcaagc   2820 agcagattac gcgcagaaaa aaaggatctc aagaagatcc tttgatcttt tctacggggt   2880
ctgacgctca gtggaacgaa aactcacgtt aagggatttt ggtcatgact agtgcttgga   2940
ttctcaccaa taaaaaacgc ccggcggcaa ccgagcgttc tgaacaaatc cagatggagt   3000
tctgaggtca ttactggatc tatcaacagg agtccaagcg agctcgatat caaattacgc   3060
cccgccctgc cactcatcgc agtactgttg taattcatta agcattctgc cgacatggaa   3120
gccatcacag acggcatgat gaacctgaat cgccagcggc atcagcacct tgtcgccttg   3180
cgtataatat ttgcccatgg tgaaaacggg ggcgaagaag ttgtccatat tggccacgtt   3240
taaatcaaaa ctggtgaaac tcacccaggg attggctgag acgaaaaaca tattctcaat   3300
aaacccttta gggaaatagg ccaggttttc accgtaacac gccacatctt gcgaatatat   3360
gtgtagaaac tgccggaaat cgtcgtggta ttcactccag agcgatgaaa acgtttcagt   3420
ttgctcatgg aaaacggtgt aacaagggtg aacactatcc catatcacca gctcaccgtc   3480
tttcattgcc atacgaaatt ccggatgagc attcatcagg cgggcaagaa tgtgaataaa   3540
```

-continued

```
ggccggataa aacttgtgct tattttcctt tacggtcttt aaaaaggccg taatatccag    3600
ctgaacggtc tggttatagg tacattgagc aactgactga aatgcctcaa aatgttcttt    3660
acgatgccat tgggatatat caacggtggt atatccagtg attttttcct ccattttagc    3720
ttccttagct cctgaaaatc tcgataactc aaaaaatacg cccggtagtg atcttatttc    3780
attatggtga agttggaac ctcttacgtg ccgatcaacg tctcatttc gccagatatc      3840 gacgtctaag aaaccattat tatcatgaca ttaacctata aaaataggcg tatcacgagg    3900
ccctttcgtc ttcacc                                                   3916
```

<210> SEQ ID NO 6
<211> LENGTH: 35
<212> TYPE: DNA
<213> ORGANISM: Artificial Sequence
<220> FEATURE:
<223> OTHER INFORMATION: Integration primer used to generate expression plasmids

<400> SEQUENCE: 6
cagcggggat ccatgataca tcagccagat cctac                              35

<210> SEQ ID NO 7
<211> LENGTH: 33
<212> TYPE: DNA
<213> ORGANISM: Artificial Sequence
<220> FEATURE:
<223> OTHER INFORMATION: Integration primer used to generate expression plasmids

<400> SEQUENCE: 7
cagcgactcg agcaggaaca gccaattcga gat                                33

<210> SEQ ID NO 8
<211> LENGTH: 35
<212> TYPE: DNA
<213> ORGANISM: Artificial Sequence
<220> FEATURE:
<223> OTHER INFORMATION: Integration primer used to generate expression plasmids

<400> SEQUENCE: 8
caggtcctcg agccacagag cagaaagccc tagta                              35

<210> SEQ ID NO 9
<211> LENGTH: 33
<212> TYPE: DNA
<213> ORGANISM: Artificial Sequence
<220> FEATURE:
<223> OTHER INFORMATION: Integration primer used to generate expression plasmids

<400> SEQUENCE: 9
catcgtggat ccctacataa gaacaccttt ggt                                33

<210> SEQ ID NO 10
<211> LENGTH: 35
<212> TYPE: DNA
<213> ORGANISM: Artificial Sequence
<220> FEATURE:
<223> OTHER INFORMATION: Integration primer used to generate expression plasmids

<400> SEQUENCE: 10
cagcggggat ccatgataca tcagccagat cctac                              35

<210> SEQ ID NO 11
<211> LENGTH: 83
<212> TYPE: DNA
<213> ORGANISM: Artificial Sequence
<220> FEATURE:
<223> OTHER INFORMATION: Integration primer used to generate expression plasmids

<400> SEQUENCE: 11
cagaaccgta cgggaactat gcatctctga ggaatggtct tctcctccaa caaaacacct    60
aggaggaaca gccaattcga gat    83

<210> SEQ ID NO 12
<211> LENGTH: 35
<212> TYPE: DNA
<213> ORGANISM: Artificial Sequence
<220> FEATURE:
<223> OTHER INFORMATION: Integration primer used to generate expression plasmids

<400> SEQUENCE: 12
caggtcgcgg ccgcacagag cagaaagccc tagta    35

<210> SEQ ID NO 13
<211> LENGTH: 69
<212> TYPE: DNA
<213> ORGANISM: Artificial Sequence
<220> FEATURE:
<223> OTHER INFORMATION: Integration primer used to generate expression plasmids

<400> SEQUENCE: 13
cagaacgtcg acttaagcgt aatctggaac atcgtatggg tactgcagca taagaacacc    60
tttggtgga    69

<210> SEQ ID NO 14
<211> LENGTH: 14
<212> TYPE: DNA
<213> ORGANISM: Artificial Sequence
<220> FEATURE:
<223> OTHER INFORMATION: Integration primer used to generate expression plasmids

<400> SEQUENCE: 14
gtacgggcgg cagc    14

<210> SEQ ID NO 15
<211> LENGTH: 14
<212> TYPE: DNA
<213> ORGANISM: Artificial Sequence
<220> FEATURE:
<223> OTHER INFORMATION: Integration primer used to generate expression plasmids

<400> SEQUENCE: 15
ggccgctgcc gccc    14

<210> SEQ ID NO 16
<211> LENGTH: 35
<212> TYPE: DNA
<213> ORGANISM: Artificial Sequence
<220> FEATURE:
<223> OTHER INFORMATION: Integration primer used to generate expression plasmids

<400> SEQUENCE: 16

```
tcaactcgta cgtctgaagt aattgaaggt aacgt                                35
```

<210> SEQ ID NO 17
<211> LENGTH: 35
<212> TYPE: DNA
<213> ORGANISM: Artificial Sequence
<220> FEATURE:
<223> OTHER INFORMATION: Integration primer used to generate expression
     plasmids

<400> SEQUENCE: 17

```
cagcggggat ccgttgacct tcaacaattc gacgt                                35
```

<210> SEQ ID NO 18
<211> LENGTH: 36
<212> TYPE: DNA
<213> ORGANISM: Artificial Sequence
<220> FEATURE:
<223> OTHER INFORMATION: Integration primer used to generate expression
     plasmids

<400> SEQUENCE: 18

```
gatcctaccc atacgatgtt ccagattacg cttaag                               36
```

<210> SEQ ID NO 19
<211> LENGTH: 36
<212> TYPE: DNA
<213> ORGANISM: Artificial Sequence
<220> FEATURE:
<223> OTHER INFORMATION: Integration primer used to generate expression
     plasmids

<400> SEQUENCE: 19

```
tcgacttaag cgtaatctgg aacatcgtat gggtag                               36
```

<210> SEQ ID NO 20
<211> LENGTH: 33
<212> TYPE: DNA
<213> ORGANISM: Artificial Sequence
<220> FEATURE:
<223> OTHER INFORMATION: Integration primer used to generate expression
     plasmids

<400> SEQUENCE: 20

```
cagaactcta gaagacgaat tgatcagatt ggc                                  33
```

<210> SEQ ID NO 21
<211> LENGTH: 37
<212> TYPE: DNA
<213> ORGANISM: Artificial Sequence
<220> FEATURE:
<223> OTHER INFORMATION: Integration primer used to generate expression
     plasmids

<400> SEQUENCE: 21

```
cagaacgcat gctttgtctt ggtgttgttc aggctgt                              37
```

<210> SEQ ID NO 22
<211> LENGTH: 34
<212> TYPE: DNA
<213> ORGANISM: Artificial Sequence
<220> FEATURE:
<223> OTHER INFORMATION: Integration primer used to generate expression
     plasmids

<400> SEQUENCE: 22

```
cagaacttaa ttaaccaggt ttgagtacgc ttcc                              34
```

<210> SEQ ID NO 23
<211> LENGTH: 34
<212> TYPE: DNA
<213> ORGANISM: Artificial Sequence
<220> FEATURE:
<223> OTHER INFORMATION: Integration primer used to generate expression
      plasmids

<400> SEQUENCE: 23

```
cagaacgcgg ccgcaaagga ttttcggtaa gcga                              34
```

<210> SEQ ID NO 24
<211> LENGTH: 35
<212> TYPE: DNA
<213> ORGANISM: Artificial Sequence
<220> FEATURE:
<223> OTHER INFORMATION: Integration primer used to generate expression
      plasmids

<400> SEQUENCE: 24

```
cagaaccgta cgtctgaagt aattgaaggt aacgt                             35
```

<210> SEQ ID NO 25
<211> LENGTH: 37
<212> TYPE: DNA
<213> ORGANISM: Artificial Sequence
<220> FEATURE:
<223> OTHER INFORMATION: Integration primer used to generate expression
      plasmids

<400> SEQUENCE: 25

```
cagaacttaa ttaattagtt gaccttcaac aattcga                           37
```

<210> SEQ ID NO 26
<211> LENGTH: 47
<212> TYPE: DNA
<213> ORGANISM: Artificial Sequence
<220> FEATURE:
<223> OTHER INFORMATION: Integration primer used to generate expression
      plasmids

<400> SEQUENCE: 26

```
ctgttttgtt ggaggagaag accattcctc agagatgcat agttccc                47
```

<210> SEQ ID NO 27
<211> LENGTH: 55
<212> TYPE: DNA
<213> ORGANISM: Artificial Sequence
<220> FEATURE:
<223> OTHER INFORMATION: Integration primer used to generate expression
      plasmids

<400> SEQUENCE: 27

```
gtacgggaac tatgcatctc tgaggaatgg tcttctcctc caacaaaaca gtacg       55
```